(12) United States Patent
Ashcroft et al.

(10) Patent No.: US 8,445,224 B2
(45) Date of Patent: May 21, 2013

(54) METHOD FOR ASSAYING FTO (2-OXOGLUTARATE DEPENDENT OXYGENASE) ACTIVITY

(75) Inventors: Frances Mary Ashcroft, Oxford (GB); Christopher Paul Ponting, Oxford (GB); Thomas Gerken, Oxford (GB); Christopher Joseph Schofield, Oxford (GB)

(73) Assignee: Isis Innovation Limited, Oxford (GB)

( * ) Notice: Subject to any disclaimer, the term of this patent is extended or adjusted under 35 U.S.C. 154(b) by 414 days.

(21) Appl. No.: 12/665,224

(22) PCT Filed: Jun. 20, 2008

(86) PCT No.: PCT/GB2008/002119
§ 371 (c)(1),
(2), (4) Date: May 13, 2010

(87) PCT Pub. No.: WO2008/155556
PCT Pub. Date: Dec. 24, 2008

(65) Prior Publication Data
US 2010/0216832 A1    Aug. 26, 2010

(30) Foreign Application Priority Data

Jun. 20, 2007  (GB) .................................. 0711955.5
Nov. 8, 2007  (GB) .................................. 0721944.7

(51) Int. Cl.
*C12P 1/26*    (2006.01)

(52) U.S. Cl.
USPC ............................... 435/25; 435/6.1; 435/189

(58) Field of Classification Search
USPC .............................................. 435/6.1, 25, 183
See application file for complete search history.

(56) References Cited

PUBLICATIONS

Machine translation of CN 1318370 (Oct. 24, 2001) downloaded from http://toolkit.dialog.com/intranet/cgi/present?STYLE=1360085582 4 pages.*
Gerkin et al. Science (Nov. 30, 2007) 328: 1469-1472.*
Boissel et al. Am. J. Human Genetics (2009) 85: 106-111.*
Anselme et al., "Defects in Brain Patterning and Head Morphogenesis in the Mouse Mutant *Fused toes*," Dev. Biol. 304:208-220, 2007.
Clissold et al., "JmjC: Cupin Metalloenzyme-Like Domains in Jumonji, Hairless and Phospholipase $A_2$ β," Trends Biochem. Sci. 26:7-9, 2001.
Dina et al., "Variation in FTO Contributes to Childhood Obesity and Severe Adult Obesity," Nature Genetics 39:724-726, 2007.
Dunwell et al., "Cupins: The Most Functionally Diverse Protein Superfamily?" Phytochemistry 65:7-17, 2004.
Frayling et al., "A Common Variant in the FTO Gene is Associated with Body Mass Index and Predisposes to Childhood and Adult Obesity," Science 316:889-894, 2007.
Gerken et al., "The Obesity-Associated FTO Gene Encodes a 2-Oxoglutarate-Dependent Nucleic Acid Demethylase," Science 318:1469-1472, 2007.
Goto et al., "Intracellular Signal Transduction Modulating Expression of Plasminogen Activator Inhibitor-1 in Adipocytes," Biochem. Pharmacol. 65:1907-1914, 2003.
Grotewold et al., "The *Fused toes (Ft)* Mouse Mutation Causes Anteroposterior and Dorsoventral Polydactyly," Dev. Biol. 251:129-141, 2002.
Harmon et al., "The Effect of Flavonoids on Preadipocyte Proliferation and Differentiation," FASEB J. 14:A214, 2000, abstract considered.
Hausinger, "Fe(II)/α-Ketoglutarate-Dependent Hydroxylases and Related Enzymes," Crit. Rev. Biochem. Mol. Biol. 39:21-68, 2004.
Myllylä et al., "The Role of Ascorbate in the Prolyl Hydroxylase Reaction," Biochem. Biophys. Res. Commun. 83:441-448, 1978.
Peters et al., "Cloning of Fatso (*Fto*), a Novel Gene Deleted by the Fused toes (*Ft*) Mouse Mutation," Mammalian Genome 10:983-986, 1999.
Ryle et al., "Non-Heme Iron Oxygenases," Curr. Opin. Chem. Biol. 6:193-201, 2002.
Scott et al., "A Genome-Wide Association Study of Type 2 Diabetes in Finns Detects Multiple Susceptibility Variants," Science 316:1341-1345, 2007.
Sundheim et al., "Human ABH3 Structure and Key Residues for Oxidative Demethylation to Reverse DNA/RNA Damage," Embo J. 25:3389-3397, 2006.
van der Hoeven et al. "Programmed Cell Death is Affected in the Novel Mouse Mutant *Fused toes (Ft)*," Development 120:2601-2607, 1994.
Yu et al., "Crystal Structures of Catalytic Complexes of the Oxidative DNA/RNA Repair Enzyme AlkB," Nature 439:879-884, 2006.
Zhang et al., "Expression, Purification and Characterization of 1-Aminocyclopropane-1-Carboxylate Oxidase from Tomato in *Escherichia coli*," Biochem J. 307:77-85, 1995.
International Search Report from International Application No. PCT/GB2008/002119, dated Aug. 21, 2008 (date of completion of search) and Sep. 8, 2008 (date of mailing of report).
Written Opinion from International Application No. PCT/GB2008/002119, dated Aug. 21, 2008 (date of completion of opinion) and Sep. 8, 2008 (date of mailing of opinion).
UK Search Report from UK Application No. 0711955.5, dated Sep. 21, 2007.

* cited by examiner

*Primary Examiner* — Susan Hanley
(74) *Attorney, Agent, or Firm* — Clark & Elbing LLP

(57) ABSTRACT

The present invention provides a method for assaying oxygenase activity, the method comprising monitoring oxygenase activity of FTO.

24 Claims, 10 Drawing Sheets

Compound 1

R = CO₂H, R' = H,
Pyridine-2,4-dicarboxylate (P-2,4-DC)
R = H, R' = CO₂H,
Pyridine-2,5-dicarboxylate (P-2,5-DC)

X = CH₂, R = H, 2OG
X = NH, R = H, N-oxalylglycine (NOG)
X = NH, R = CH₂Ph,
N-oxalyl-D-phenylalanine (NOFD)

SEQUENCE LISTING

```
<160> NUMBER OF SEQ ID NOS: 15

<210> SEQ ID NO 1
<211> LENGTH: 505
<212> TYPE: PRT
<213> ORGANISM: Homo sapiens
<220> FEATURE:
<221> NAME/KEY: SITE
<222> LOCATION: (1)..(77)
<223> OTHER INFORMATION: N-terminal extension
<220> FEATURE:
<221> NAME/KEY: SITE
<222> LOCATION: (78)..(118)
<223> OTHER INFORMATION: Nucleotide-recognition lid
<220> FEATURE:
<221> NAME/KEY: SITE
<222> LOCATION: (119)..(323)
<223> OTHER INFORMATION: catalytic core
<220> FEATURE:
<221> NAME/KEY: SITE
<222> LOCATION: (203)..(203)
<223> OTHER INFORMATION: putative substrate binding residue
<220> FEATURE:
<221> NAME/KEY: SITE
```

```
<222> LOCATION: (228)..(233)
<223> OTHER INFORMATION: putative substrate binding residue
<220> FEATURE:
<221> NAME/KEY: SITE
<222> LOCATION: (231)..(231)
<223> OTHER INFORMATION: Fe(II) binding residue
<220> FEATURE:
<221> NAME/KEY: SITE
<222> LOCATION: (233)..(233)
<223> OTHER INFORMATION: Fe(II) binding residue
<220> FEATURE:
<221> NAME/KEY: SITE
<222> LOCATION: (242)..(242)
<223> OTHER INFORMATION: residue lining O2 binding cavity
<220> FEATURE:
<221> NAME/KEY: SITE
<222> LOCATION: (269)..(269)
<223> OTHER INFORMATION: residue lining O2 binding cavity
<220> FEATURE:
<221> NAME/KEY: SITE
<222> LOCATION: (276)..(276)
<223> OTHER INFORMATION: putative substrate binding residue
<220> FEATURE:
<221> NAME/KEY: SITE
<222> LOCATION: (297)..(297)
<223> OTHER INFORMATION: residue lining O2 binding cavity
<220> FEATURE:
<221> NAME/KEY: SITE
<222> LOCATION: (307)..(307)
<223> OTHER INFORMATION: Fe(II) binding residue
<220> FEATURE:
<221> NAME/KEY: SITE
<222> LOCATION: (316)..(316)
<223> OTHER INFORMATION: 2-OG 5' carboxylate binding residue
<220> FEATURE:
<221> NAME/KEY: SITE
<222> LOCATION: (322)..(322)
<223> OTHER INFORMATION: putative substrate binding residue

<400> SEQUENCE: 1

Met Lys Arg Thr Pro Thr Ala Glu Glu Arg Glu Ala Lys Lys
1               5                   10                  15

Leu Arg Leu Leu Glu Glu Leu Glu Asp Thr Trp Leu Pro Tyr Leu Thr
                20                  25                  30

Pro Lys Asp Asp Glu Phe Tyr Gln Gln Trp Gln Leu Lys Tyr Pro Lys
                35                  40                  45

Leu Ile Leu Arg Glu Ala Ser Ser Val Ser Glu Glu Leu His Lys Glu
        50                  55                  60

Val Gln Glu Ala Phe Leu Thr Leu His Lys His Gly Cys Leu Phe Arg
65                  70                  75                  80

Asp Leu Val Arg Ile Gln Gly Lys Asp Leu Leu Thr Pro Val Ser Arg
                85                  90                  95

Ile Leu Ile Gly Asn Pro Gly Cys Thr Tyr Lys Tyr Leu Asn Thr Arg
            100                 105                 110

Leu Phe Thr Val Pro Trp Pro Val Lys Gly Ser Asn Ile Lys His Thr
        115                 120                 125

Glu Ala Glu Ile Ala Ala Ala Cys Glu Thr Phe Leu Lys Leu Asn Asp
    130                 135                 140

Tyr Leu Gln Ile Glu Thr Ile Gln Ala Leu Glu Glu Leu Ala Ala Lys
145                 150                 155                 160

Glu Lys Ala Asn Glu Asp Ala Val Pro Leu Cys Met Ser Ala Asp Phe
                165                 170                 175

Pro Arg Val Gly Met Gly Ser Ser Tyr Asn Gly Gln Asp Glu Val Asp
            180                 185                 190

Ile Lys Ser Arg Ala Ala Tyr Asn Val Thr Leu Leu Asn Phe Met Asp
        195                 200                 205
```

```
Pro Gln Lys Met Pro Tyr Leu Lys Glu Glu Pro Tyr Phe Gly Met Gly
    210                 215                 220
Lys Met Ala Val Ser Trp His His Asp Glu Asn Leu Val Asp Arg Ser
225                 230                 235                 240
Ala Val Ala Val Tyr Ser Tyr Ser Cys Glu Gly Pro Glu Glu Glu Ser
                245                 250                 255
Glu Asp Asp Ser His Leu Glu Gly Arg Asp Pro Asp Ile Trp His Val
                260                 265                 270
Gly Phe Lys Ile Ser Trp Asp Ile Glu Thr Pro Gly Leu Ala Ile Pro
            275                 280                 285
Leu His Gln Gly Asp Cys Tyr Phe Met Leu Asp Asp Leu Asn Ala Thr
    290                 295                 300
His Gln His Cys Val Leu Ala Gly Ser Gln Pro Arg Phe Ser Ser Thr
305                 310                 315                 320
His Arg Val Ala Glu Cys Ser Thr Gly Thr Leu Asp Tyr Ile Leu Gln
                325                 330                 335
Arg Cys Gln Leu Ala Leu Gln Asn Val Cys Asp Val Asp Asn Asp
                340                 345                 350
Asp Val Ser Leu Lys Ser Phe Glu Pro Ala Val Leu Lys Gln Gly Glu
            355                 360                 365
Glu Ile His Asn Glu Val Glu Phe Glu Trp Leu Arg Gln Phe Trp Phe
    370                 375                 380
Gln Gly Asn Arg Tyr Arg Lys Cys Thr Asp Trp Trp Cys Gln Pro Met
385                 390                 395                 400
Ala Gln Leu Glu Ala Leu Trp Lys Lys Met Glu Gly Val Thr Asn Ala
                405                 410                 415
Val Leu His Glu Val Lys Arg Glu Gly Leu Pro Val Gln Gln Arg Asn
            420                 425                 430
Glu Ile Leu Thr Ala Ile Leu Ala Ser Leu Thr Ala Arg Gln Asn Leu
    435                 440                 445
Arg Arg Glu Trp His Ala Arg Cys Gln Ser Arg Ile Ala Arg Thr Leu
    450                 455                 460
Pro Ala Asp Gln Lys Pro Glu Cys Arg Pro Tyr Trp Glu Lys Asp Asp
465                 470                 475                 480
Ala Ser Met Pro Leu Pro Phe Asp Leu Thr Asp Ile Val Ser Glu Leu
                485                 490                 495
Arg Gly Gln Leu Leu Glu Ala Lys Pro
            500                 505

<210> SEQ ID NO 2
<211> LENGTH: 505
<212> TYPE: PRT
<213> ORGANISM: Pan troglodytes
<220> FEATURE:
<221> NAME/KEY: SITE
<222> LOCATION: (78)..(118)
<223> OTHER INFORMATION: Nucleotide-recognition lid
<220> FEATURE:
<221> NAME/KEY: SITE
<222> LOCATION: (119)..(323)
<223> OTHER INFORMATION: catalytic core

<400> SEQUENCE: 2

Met Lys Arg Thr Pro Thr Ala Glu Glu Arg Arg Glu Ala Lys Lys
1               5                   10                  15

Leu Arg Leu Leu Glu Glu Leu Asp Thr Trp Leu Pro Tyr Leu Thr
            20                  25                  30

Pro Lys Asp Asp Glu Phe Tyr Gln Gln Trp Gln Leu Lys Tyr Pro Lys
```

```
                35                  40                  45
Leu Ile Leu Arg Glu Ala Ser Ser Val Ser Glu Glu Leu His Lys Glu
 50                  55                  60

Val Gln Glu Ala Phe Leu Thr Leu His Lys His Gly Cys Leu Phe Arg
 65                  70                  75                  80

Asp Leu Val Arg Ile Gln Gly Lys Asp Leu Leu Thr Pro Val Ser Arg
                 85                  90                  95

Ile Leu Ile Gly Asn Pro Gly Cys Thr Tyr Lys Tyr Leu Asn Thr Arg
                100                 105                 110

Leu Phe Thr Val Pro Trp Pro Val Lys Gly Ser Asn Ile Lys His Thr
                115                 120                 125

Glu Ala Glu Ile Ala Ala Cys Glu Thr Phe Leu Lys Leu Asn Asp
130                 135                 140

Tyr Leu Gln Ile Glu Thr Ile Gln Ala Leu Glu Glu Leu Ala Ala Lys
145                 150                 155                 160

Glu Lys Ala Asn Glu Asp Ala Val Pro Leu Cys Met Ser Ala Asp Phe
                165                 170                 175

Pro Arg Val Gly Met Gly Ser Ser Tyr Asn Gly Gln Asp Glu Val Asp
                180                 185                 190

Ile Lys Ser Arg Ala Ala Tyr Asn Val Thr Leu Leu Asn Phe Met Asp
                195                 200                 205

Pro Gln Lys Met Pro Tyr Leu Lys Glu Pro Tyr Phe Gly Met Gly
                210                 215                 220

Lys Met Ala Val Ser Trp His His Asp Glu Asn Leu Val Asp Arg Ser
225                 230                 235                 240

Ala Val Ala Val Tyr Ser Tyr Ser Cys Glu Gly Pro Glu Glu Ser
                245                 250                 255

Glu Asp Asp Ser His Leu Glu Gly Arg Asp Pro Asp Ile Trp His Val
                260                 265                 270

Gly Phe Lys Ile Ser Trp Asp Ile Glu Thr Pro Gly Leu Ala Ile Pro
                275                 280                 285

Leu His Gln Gly Asp Cys Tyr Phe Met Leu Asp Asp Leu Asn Ala Thr
                290                 295                 300

His Gln His Cys Val Leu Ala Gly Ser Gln Pro Arg Phe Ser Ser Thr
305                 310                 315                 320

His Arg Val Ala Glu Cys Ser Thr Gly Thr Leu Asp Tyr Ile Leu Gln
                325                 330                 335

Arg Cys Gln Leu Ala Leu Gln Asn Val Cys Asp Asp Val Asp Asn Asp
                340                 345                 350

Asp Val Ser Leu Lys Ser Phe Glu Pro Ala Val Leu Lys Gln Gly Glu
                355                 360                 365

Glu Ile His Asn Glu Val Glu Phe Glu Trp Leu Arg Gln Phe Trp Phe
                370                 375                 380

Gln Gly Asn Arg Tyr Arg Lys Cys Thr Asp Trp Cys Gln Pro Met
385                 390                 395                 400

Ala Gln Leu Glu Ala Leu Trp Lys Lys Met Glu Gly Val Thr Asn Ala
                405                 410                 415

Val Leu His Glu Val Lys Gly Glu Gly Leu Pro Met Glu Gln Arg Asn
                420                 425                 430

Glu Ile Leu Thr Ala Ile Leu Ala Ser Leu Thr Ala Arg Gln Asn Leu
                435                 440                 445

Arg Arg Glu Trp His Ala Arg Cys Gln Ser Arg Ile Ala Arg Thr Leu
450                 455                 460
```

```
Pro Ala Asp Gln Lys Pro Glu Cys Arg Pro Tyr Trp Glu Lys Asp Asp
465                 470                 475                 480

Ala Ser Met Pro Leu Pro Phe Asp Leu Thr Asp Ile Val Ser Glu Leu
                485                 490                 495

Arg Gly Gln Leu Leu Glu Ala Lys Pro
            500                 505

<210> SEQ ID NO 3
<211> LENGTH: 515
<212> TYPE: PRT
<213> ORGANISM: Macaca mulatta
<220> FEATURE:
<221> NAME/KEY: SITE
<222> LOCATION: (88)..(128)
<223> OTHER INFORMATION: Nucleotide-recognition lid
<220> FEATURE:
<221> NAME/KEY: SITE
<222> LOCATION: (129)..(333)
<223> OTHER INFORMATION: catalytic core

<400> SEQUENCE: 3

Met Ala Pro Asp Gly Ser Arg Thr Leu Arg Glu Leu His Ala Gly Gly
1               5                   10                  15

Gly Val Gln Gly Glu Gly Ile Tyr Ala Ala Cys Gly Gly Gly Gly Gly
            20                  25                  30

Phe Ser Gly Ser Met Lys Arg Thr Pro Thr Ala Glu Glu Arg Glu Arg
        35                  40                  45

Glu Ala Lys Trp Gln Leu Lys Tyr Pro Lys Leu Ile Leu Arg Glu Ala
    50                  55                  60

Ser Ser Val Ser Glu Glu Leu His Lys Glu Val Gln Glu Ala Phe Leu
65                  70                  75                  80

Thr Leu His Lys His Gly Cys Leu Phe Arg Asp Leu Val Arg Ile Gln
                85                  90                  95

Gly Lys Asp Leu Leu Thr Pro Val Ser Arg Ile Leu Ile Gly Asn Pro
            100                 105                 110

Gly Cys Thr Tyr Lys Tyr Leu Asn Thr Arg Leu Phe Thr Val Pro Trp
        115                 120                 125

Pro Val Lys Gly Ser Asn Ile Lys Tyr Pro Glu Ala Glu Ile Ala Ala
    130                 135                 140

Ala Cys Glu Thr Phe Leu Lys Leu Asn Asp Tyr Leu Gln Ile Glu Thr
145                 150                 155                 160

Ile Gln Ala Leu Glu Glu Leu Ala Ala Lys Glu Lys Ala Asn Glu Asp
                165                 170                 175

Ala Val Pro Leu Cys Met Ser Ala Asp Phe Pro Arg Val Gly Met Gly
            180                 185                 190

Ser Ser Tyr Asp Gly Gln Asp Glu Val Asp Ile Lys Ser Arg Ala Ala
        195                 200                 205

Tyr Asn Val Thr Leu Leu Asn Phe Met Asp Pro Gln Lys Met Pro Tyr
    210                 215                 220

Leu Lys Glu Glu Pro Tyr Phe Gly Met Gly Lys Met Ala Val Ser Trp
225                 230                 235                 240

His His Asp Glu Asn Leu Val Asp Arg Ser Ala Val Ala Val Tyr Ser
                245                 250                 255

Tyr Ser Cys Glu Gly Pro Glu Glu Ser Asp Asp Ser His Phe
            260                 265                 270

Glu Gly Arg Asp Pro Asp Ile Trp His Val Gly Phe Lys Ile Ser Trp
        275                 280                 285

Asp Ile Glu Thr Pro Gly Leu Ala Ile Pro Leu His Gln Gly Asp Cys
```

-continued

```
                290                 295                 300
Tyr Phe Met Leu Asp Asp Leu Asn Ala Thr His Gln His Cys Val Leu
305                 310                 315                 320

Ala Gly Ser Gln Pro Arg Phe Ser Ser Thr His Arg Val Ala Glu Cys
                325                 330                 335

Ser Thr Gly Thr Leu Asp Tyr Ile Leu Gln Arg Cys Gln Leu Ala Leu
                340                 345                 350

Gln Asn Val Arg Asp Val Asp Asn Gly Asp Val Ser Leu Lys Ser
                355                 360                 365

Phe Glu Pro Ala Val Leu Lys Gln Gly Glu Ile His Asn Glu Val
370                 375                 380

Glu Phe Glu Trp Leu Arg Gln Phe Trp Phe Gln Gly Asn Arg Tyr Arg
385                 390                 395                 400

Lys Cys Thr Asp Trp Trp Cys Gln Pro Met Ala Gln Leu Glu Ala Leu
                405                 410                 415

Trp Lys Lys Met Glu Gly Val Thr Asn Ala Val Leu His Glu Val Lys
                420                 425                 430

Arg Glu Gly Leu Pro Val Glu Gln Arg Asn Glu Ile Leu Thr Ala Ile
                435                 440                 445

Leu Ala Ser Leu Thr Ala Arg Gln Asn Leu Arg Arg Glu Trp His Ala
450                 455                 460

Arg Cys Gln Ser Arg Ile Ala Arg Thr Leu Pro Ala Asp Gln Lys Pro
465                 470                 475                 480

Glu Cys Arg Pro Tyr Trp Glu Lys Asp Val Ser Met Pro Leu Pro
                485                 490                 495

Phe Asp Leu Thr Asp Ile Val Ser Glu Leu Arg Gly Gln Leu Leu Glu
                500                 505                 510

Ala Lys Pro
515

<210> SEQ ID NO 4
<211> LENGTH: 571
<212> TYPE: PRT
<213> ORGANISM: Canis familiaris
<220> FEATURE:
<221> NAME/KEY: SITE
<222> LOCATION: (145)..(185)
<223> OTHER INFORMATION: Nucleotide-recognition lid
<220> FEATURE:
<221> NAME/KEY: SITE
<222> LOCATION: (186)..(389)
<223> OTHER INFORMATION: catalytic core

<400> SEQUENCE: 4

Met Val Val Pro Ala Ala Leu Thr Glu Asn Gly Ala Gly Arg Glu Gln
1               5                   10                  15

Asp Ala Glu Arg Thr Thr Ser Arg Arg Gly Pro Gly Arg Ile
                20                  25                  30

Tyr Ala Ala Arg Ser Gly Glu Gly Gly Cys Ser Gly Ser Met Lys Arg
                35                  40                  45

Thr Pro Thr Ala Glu Glu Arg Glu Arg Glu Ala Lys Lys Leu Arg Leu
                50                  55                  60

Leu Glu Glu Leu Glu Asp Thr Trp Leu Pro Tyr Leu Thr Pro Lys Asp
65                  70                  75                  80

Asp Glu Phe Tyr Gln Gln Met Glu Thr Ile Trp Tyr Met Ile Ala Tyr
                85                  90                  95

Thr Leu Leu Lys Gln Leu Leu Ser Leu Thr Ala Ser Trp Gln Leu Lys
                100                 105                 110
```

```
Tyr Pro Lys Leu Ile Leu Arg Glu Ala Gly Ser Val Pro Glu Asp Leu
        115                 120                 125

His Lys Glu Val Gln Glu Ala Phe Leu Thr Leu His Lys His Gly Cys
    130                 135                 140

Phe Phe Arg Asp Leu Val Arg Ile Gln Gly Lys Asp Leu Leu Thr Pro
145                 150                 155                 160

Val Ser Arg Ile Leu Ile Gly Asn Pro Gly Cys Thr Tyr Lys Tyr Leu
                165                 170                 175

Asn Thr Arg Leu Phe Thr Val Pro Trp Pro Val Lys Gly Ala Ser Thr
            180                 185                 190

Lys Tyr Asp Glu Ala Gly Ile Ala Ala Cys Gln Thr Phe Leu Lys
            195                 200                 205

Leu Asn Asp Tyr Leu Gln Ile Glu Thr Ile Gln Ala Leu Glu Glu Leu
        210                 215                 220

Ala Cys Lys Glu Lys Ser Asn Ile Asp Ala Val Pro Val Cys Ile Gly
225                 230                 235                 240

Pro Asp Phe Pro Arg Val Gly Met Gly Ser Phe Asp Gly Gln Asp Glu
                245                 250                 255

Leu Asp Ile Lys Asn Arg Ala Ala Tyr Asn Val Thr Leu Leu Asn Phe
            260                 265                 270

Met Asp Pro Gln Lys Met Pro Tyr Leu Lys Glu Glu Pro Tyr Phe Gly
        275                 280                 285

Met Gly Lys Met Ala Val Ser Trp His His Asp Glu Asn Leu Val Glu
        290                 295                 300

Arg Ser Ala Val Ala Val Tyr Ser Tyr Ser Cys Glu Gly Pro Glu Glu
305                 310                 315                 320

Glu Ser Glu Asp Asp Pro Gln Leu Glu Gly Arg Asp Pro Asp Thr Trp
                325                 330                 335

His Val Gly Phe Lys Ile Ser Trp Asp Ile Glu Thr Pro Gly Leu Ala
            340                 345                 350

Ile Pro Leu His Gln Gly Asp Cys Tyr Phe Met Leu Asp Asp Leu Asn
        355                 360                 365

Ala Thr His Gln His Cys Val Leu Ala Gly Leu Pro Pro Arg Phe Ser
        370                 375                 380

Ser Thr His Arg Val Ala Glu Cys Ser Thr Gly Thr Leu Asp Tyr Ile
385                 390                 395                 400

Leu Gln Arg Cys Gln Leu Ala Leu Gln Asn Val Arg Asp Glu Ala Asp
                405                 410                 415

Asn Gly Asp Val Ser Leu Lys Ser Phe Glu Pro Val Val Leu Lys Gln
            420                 425                 430

Gly Glu Glu Ile His Asn Glu Val Glu Phe Glu Trp Leu Arg Gln Tyr
        435                 440                 445

Trp Phe Gln Gly Asn Arg Tyr Arg Lys Cys Thr Asp Trp Trp Cys Gln
450                 455                 460

Pro Met Thr Gln Leu Glu Gly Leu Trp Lys Lys Met Glu Gly Val Thr
465                 470                 475                 480

Asn Ala Val Leu His Glu Val Arg Arg Glu Gly Val Pro Val Glu Gln
                485                 490                 495

Arg Asn Glu Ile Leu Thr Ala Ile Leu Ala Leu Leu Thr Arg Gln
            500                 505                 510

Asn Leu Arg Arg Glu Trp His Ala Arg Cys Gln Ser Arg Ile Ala Arg
        515                 520                 525

Thr Leu Pro Val Asp Gln Lys Pro Glu Cys Arg Pro Tyr Trp Glu Lys
```

```
                530                 535                 540
Asp Asp Pro Ser Met Pro Leu Pro Phe Asp Leu Thr Asp Ile Val Ser
545                 550                 555                 560

Glu Leu Arg Gly Leu Leu Leu Glu Ala Lys Pro
                565                 570
```

<210> SEQ ID NO 5
<211> LENGTH: 505
<212> TYPE: PRT
<213> ORGANISM: Bos taurus
<220> FEATURE:
<221> NAME/KEY: SITE
<222> LOCATION: (63)..(103)
<223> OTHER INFORMATION: Nucleotide-recognition lid
<220> FEATURE:
<221> NAME/KEY: SITE
<222> LOCATION: (104)..(308)
<223> OTHER INFORMATION: catalytic core

<400> SEQUENCE: 5

```
Met Lys Arg Thr Pro Thr Ala Glu Glu Arg Glu Ala Lys Lys
1               5                   10                  15

Leu Arg Leu Leu Glu Glu Leu Gly Asp Thr Trp Leu Pro Tyr Leu Thr
                20                  25                  30

Pro Lys Asp Asp Glu Phe Tyr Gln Gln Trp Gln Leu Lys Tyr Pro Lys
                35                  40                  45

Leu Ile Leu Arg Glu Ala Ala Ser Val Pro Glu Leu Leu His Lys Glu
50                  55                  60

Val Gln Gln Ala Phe Leu Thr Leu His Lys His Gly Cys Leu Phe Arg
65                  70                  75                  80

Asp Leu Val Arg Ile Gln Gly Lys Asp Leu Leu Thr Pro Val Ser Arg
                85                  90                  95

Ile Leu Ile Gly Asn Pro Gly Cys Thr Tyr Lys Tyr Leu Asn Thr Arg
                100                 105                 110

Leu Phe Thr Val Pro Trp Pro Val Lys Gly Ser Asp Ala Lys Tyr Asn
                115                 120                 125

Glu Ala Glu Ile Ala Ala Cys Gln Thr Phe Leu Lys Leu Asn Ser
130                 135                 140

Tyr Leu Gln Val Glu Thr Ile Gln Ala Leu Glu Glu Leu Ala Ala Lys
145                 150                 155                 160

Glu Lys Ala Asn Ile Asp Ala Val Pro Val Cys Ile Gly Pro Asp Phe
                165                 170                 175

Pro Arg Val Gly Met Gly Ser Ser Phe Asp Gly His Asp Glu Ile Asp
                180                 185                 190

Met Lys Asn Arg Ala Ala Tyr Asn Val Thr Leu Leu Asn Phe Met Asp
                195                 200                 205

Pro Gln Lys Met Pro Tyr Leu Lys Glu Glu Pro Tyr Phe Gly Met Gly
210                 215                 220

Lys Met Ala Val Ser Trp His His Asp Glu Asn Leu Val Asp Arg Ser
225                 230                 235                 240

Ala Val Ala Val Tyr Ser Tyr Ser Cys Glu Gly Pro Glu Glu Glu Ser
                245                 250                 255

Glu Asp Asp Pro Gln Leu Glu Gly Arg Asp Pro Asp Ile Trp His Val
                260                 265                 270

Gly Phe Lys Ile Ser Trp Asp Ile Glu Thr Pro Gly Leu Ala Ile Pro
                275                 280                 285

Leu His Gln Gly Asp Cys Tyr Phe Met Leu Asp Asp Leu Asn Ala Thr
290                 295                 300
```

His Gln His Cys Val Leu Ala Gly Leu Pro Pro Arg Phe Ser Ser Thr
305                 310                 315                 320

His Arg Val Ala Glu Cys Ser Thr Gly Thr Leu Glu Tyr Ile Leu Gln
                325                 330                 335

Arg Cys Gln Val Ala Leu Gln Asn Val Arg Glu Glu Ala Asp Asn Gly
                340                 345                 350

Glu Ile Ser Leu Lys Ser Leu Glu Ser Val Val Leu Lys Gln Gly Glu
                355                 360                 365

Glu Ile His Asn Glu Val Glu Phe Glu Trp Leu Arg Gln Phe Trp Phe
            370                 375                 380

Gln Gly Ser Arg Tyr Lys Lys Cys Thr Asp Trp Trp Cys Gln Pro Met
385                 390                 395                 400

Ser Gln Leu Glu Glu Met Trp Arg Lys Met Glu Trp Leu Thr Ser Ala
                405                 410                 415

Val Leu Arg Glu Val Arg Arg Glu Gly Val Pro Met Glu Gln Lys Asn
                420                 425                 430

Glu Met Leu Thr Ser Ile Leu Ala Ser Ile Thr Thr Arg Gln Asn Leu
                435                 440                 445

Arg Arg Glu Trp His Ala Arg Cys Gln Ser Arg Ile Ala Arg Thr Leu
            450                 455                 460

Pro Ala Asp Gln Lys Pro Glu Cys Arg Pro Tyr Trp Glu Lys Gly Asp
465                 470                 475                 480

Pro Ser Met Pro Leu Pro Phe Asp Leu Thr Glu Ile Val Ser Glu Leu
                485                 490                 495

Arg Gly Leu Leu Leu Glu Thr Arg Pro
                500                 505

<210> SEQ ID NO 6
<211> LENGTH: 482
<212> TYPE: PRT
<213> ORGANISM: Monodelphis domestica
<220> FEATURE:
<221> NAME/KEY: SITE
<222> LOCATION: (58)..(98)
<223> OTHER INFORMATION: Nucleotide-recognition lid
<220> FEATURE:
<221> NAME/KEY: SITE
<222> LOCATION: (99)..(300)
<223> OTHER INFORMATION: catalytic core

<400> SEQUENCE: 6

Met Gly Val Gly Arg Ala Gly Ser Arg Ser Pro Asp Lys Gln Gly Gln
1               5                   10                  15

Asp Leu Gly His Gln Trp Gln Glu Asn Tyr Ser Lys Leu Ile Leu Arg
            20                  25                  30

Glu Ala Ser Ser Ile Pro Glu Leu Leu His Lys Glu Val Gln Gln Ala
        35                  40                  45

Phe Leu Ile Leu Arg Lys His Gly Cys Leu Phe Gln Asp Leu Val Arg
    50                  55                  60

Ile Lys Gly Lys Asn Leu Leu Thr Pro Val Ser Arg Leu Leu Ile Gly
65              70                  75                  80

Asn Pro Gly Tyr Thr Tyr Lys Tyr Leu Asn Ser Arg Leu Phe Thr Val
                85                  90                  95

Pro Trp Pro Met Glu Gly Ser Asn Ile Lys Tyr Ser Lys Asp Glu Ile
                100                 105                 110

Phe Ala Ala Cys Arg Ala Phe Phe Lys Leu Asn Asp Tyr Leu Arg Lys
            115                 120                 125

-continued

Asp Thr Ile Gln Ala Leu Asp Lys Leu His Leu Ile Lys Ser Lys Asp
130                 135                 140

Ser Glu Asp Ser Ala Val Phe Gly Met Val Pro Glu Leu Ser Lys Asn
145                 150                 155                 160

Ile Leu Asn Val Gly His Asp Met Glu Leu Lys Lys Arg Thr Thr Tyr
                165                 170                 175

Asn Leu Thr Leu Leu Asn Tyr Met Asp Pro Gln Glu Met Ser Tyr Leu
            180                 185                 190

Lys Glu Glu Pro Tyr Phe Gly Met Gly Lys Met Ala Val Ser Trp His
        195                 200                 205

His Asp Glu Asn Leu Val Glu Arg Ser Thr Val Ala Val Tyr Ser Tyr
210                 215                 220

Asn Cys Glu Gly Pro Glu Val Leu Asp Asp Glu Leu Ser Pro Glu
225                 230                 235                 240

Gly Arg Asn Pro Ala Val Trp His Val Gly Leu Lys Ile Ala Trp Asp
                245                 250                 255

Ile Lys Thr Pro Gly Leu Ala Val Pro Leu His Gln Gly Asp Cys Tyr
            260                 265                 270

Leu Met Leu Asp Asn Leu Asn Ser Thr His Gln His Cys Val Leu Ala
        275                 280                 285

Gly Leu Gln Pro Arg Phe Ser Ser Thr His Arg Val Ala Glu Cys Ser
290                 295                 300

Ala Gly Thr Leu Asp Tyr Ile Phe Lys Gln Cys His Leu Ala Leu Gln
305                 310                 315                 320

Asn Val Lys Asp Asp Thr Glu Pro Arg Thr Val His Leu Arg Ser Met
                325                 330                 335

Glu Ser Ser Val Ile Lys Gln Gly Glu Ile His Asn Glu Val Glu
            340                 345                 350

Phe Glu Trp Leu Arg Gln Phe Trp Phe His Gly His Arg Tyr Lys Lys
        355                 360                 365

Cys Thr Asp Trp Trp Gln Leu Pro Met Ser Glu Leu Glu Gly Leu Trp
370                 375                 380

Lys Lys Met Glu Cys Val Thr Asn Ala Val Leu Asp Glu Ile Arg Lys
385                 390                 395                 400

Glu Arg Trp Pro Met Glu Gln Lys Asn Glu Ile Ile Thr Asp Leu Leu
                405                 410                 415

Ala Leu Leu Thr Thr Arg Gln Glu Leu Arg Met Glu Trp Cys Met Arg
            420                 425                 430

Cys Gln Ser Arg Ile Ala Gln Asn Leu Pro Glu Asp Gln Arg Pro Ile
        435                 440                 445

Cys Trp Pro Tyr Trp Glu Asp Glu Asp Pro Glu Met Pro Leu Pro Phe
450                 455                 460

Asp Leu Ser Asn Ile Ile Ser Glu Leu Gln Gly His Leu Pro Glu Thr
465                 470                 475                 480

Lys Ser

<210> SEQ ID NO 7
<211> LENGTH: 502
<212> TYPE: PRT
<213> ORGANISM: Mus musculus
<220> FEATURE:
<221> NAME/KEY: SITE
<222> LOCATION: (78)..(118)
<223> OTHER INFORMATION: Nucleotide-recognition lid
<220> FEATURE:
<221> NAME/KEY: SITE
<222> LOCATION: (119)..(320)

<223> OTHER INFORMATION: catalytic core

<400> SEQUENCE: 7

```
Met Lys Arg Val Gln Thr Ala Glu Glu Arg Glu Ala Lys Lys
1               5                   10                  15

Leu Arg Leu Leu Glu Glu Leu Glu Asp Thr Trp Leu Pro Tyr Leu Thr
            20                  25                  30

Pro Lys Asp Asp Glu Phe Tyr Gln Gln Trp Gln Leu Lys Tyr Pro Lys
        35                  40                  45

Leu Val Phe Arg Glu Ala Gly Ser Ile Pro Glu Glu Leu His Lys Glu
    50                  55                  60

Val Pro Glu Ala Phe Leu Thr Leu His Lys His Gly Cys Leu Phe Arg
65                  70                  75                  80

Asp Val Val Arg Ile Gln Gly Lys Asp Val Leu Thr Pro Val Ser Arg
                85                  90                  95

Ile Leu Ile Gly Asp Pro Gly Cys Thr Tyr Lys Tyr Leu Asn Thr Arg
            100                 105                 110

Leu Phe Thr Val Pro Trp Pro Val Lys Gly Cys Thr Val Lys Tyr Thr
        115                 120                 125

Glu Ala Glu Ile Ala Ala Ala Cys Gln Thr Phe Leu Lys Leu Asn Asp
    130                 135                 140

Tyr Leu Gln Val Glu Thr Ile Gln Ala Leu Glu Glu Leu Ala Val Arg
145                 150                 155                 160

Glu Lys Ala Asn Glu Asp Ala Val Pro Leu Cys Met Ala Glu Phe Pro
                165                 170                 175

Arg Ala Gly Val Gly Pro Ser Cys Asp Asp Glu Val Asp Leu Lys Ser
            180                 185                 190

Arg Ala Ala Tyr Asn Val Thr Leu Leu Asn Phe Met Asp Pro Gln Lys
        195                 200                 205

Met Pro Tyr Leu Lys Glu Glu Pro Tyr Phe Gly Met Gly Lys Met Ala
    210                 215                 220

Val Ser Trp His His Asp Glu Asn Leu Val Asp Arg Ser Ala Val Ala
225                 230                 235                 240

Val Tyr Ser Tyr Ser Cys Glu Gly Ser Glu Asp Ser Glu Asp Glu
                245                 250                 255

Ser Ser Phe Glu Gly Arg Asp Pro Asp Thr Trp His Val Gly Phe Lys
            260                 265                 270

Ile Ser Trp Asp Ile Glu Thr Pro Gly Leu Thr Ile Pro Leu His Gln
        275                 280                 285

Gly Asp Cys Tyr Phe Met Leu Asp Asp Leu Asn Ala Thr His Gln His
    290                 295                 300

Cys Val Leu Ala Gly Ser Gln Pro Arg Phe Ser Ser Thr His Arg Val
305                 310                 315                 320

Ala Glu Cys Ser Thr Gly Thr Leu Asp Tyr Ile Leu Glu Arg Cys Gln
                325                 330                 335

Leu Ala Leu Gln Asn Val Leu Asn Asp Ser Asp Gly Asp Val Ser
            340                 345                 350

Leu Lys Ser Phe Asp Pro Ala Val Leu Lys Gln Gly Glu Glu Ile His
        355                 360                 365

Asn Glu Val Glu Phe Glu Trp Leu Arg Gln Phe Trp Phe Gln Gly Ser
    370                 375                 380

Arg Tyr Lys Leu Cys Thr Asp Trp Trp Cys Glu Pro Met Thr His Leu
385                 390                 395                 400

Glu Gly Leu Trp Lys Lys Met Glu Ser Val Thr Asn Ala Val Leu Arg
```

-continued

```
                405                 410                 415
Glu Val Lys Arg Glu Gly Leu Pro Val Glu Gln Arg Ser Glu Ile Leu
            420                 425                 430

Ser Ala Ile Leu Val Pro Leu Thr Val Arg Gln Asn Leu Arg Lys Glu
            435                 440                 445

Trp His Ala Arg Cys Gln Ser Arg Val Val Arg Thr Leu Pro Ala Gln
            450                 455                 460

Gln Lys Pro Asp Cys Arg Pro Tyr Trp Glu Lys Asp Pro Ser Met
465                 470                 475                 480

Pro Leu Pro Phe Asp Leu Thr Asp Val Val Ser Glu Leu Arg Gly Gln
            485                 490                 495

Leu Leu Glu Ala Arg Ser
            500

<210> SEQ ID NO 8
<211> LENGTH: 502
<212> TYPE: PRT
<213> ORGANISM: Mus musculus
<220> FEATURE:
<221> NAME/KEY: SITE
<222> LOCATION: (78)..(118)
<223> OTHER INFORMATION: Nucleotide-recognition lid
<220> FEATURE:
<221> NAME/KEY: SITE
<222> LOCATION: (119)..(320)
<223> OTHER INFORMATION: catalytic core

<400> SEQUENCE: 8

Met Lys Arg Val Gln Thr Ala Glu Glu Arg Arg Glu Ala Lys Lys
1               5                   10                  15

Leu Arg Leu Leu Glu Glu Leu Glu Asp Thr Trp Leu Pro Tyr Leu Thr
            20                  25                  30

Pro Lys Asp Asp Glu Phe Tyr Gln Gln Trp Gln Leu Lys Tyr Pro Lys
            35                  40                  45

Leu Val Phe Arg Glu Ala Gly Ser Ile Pro Glu Glu Leu His Lys Glu
        50                  55                  60

Val Pro Glu Ala Phe Leu Thr Leu His Lys His Gly Cys Leu Phe Arg
65                  70                  75                  80

Asp Val Val Arg Ile Gln Gly Lys Asp Val Leu Thr Pro Val Ser Arg
                85                  90                  95

Ile Leu Ile Gly Asp Pro Gly Cys Thr Tyr Lys Tyr Leu Asn Thr Arg
            100                 105                 110

Leu Phe Thr Val Pro Trp Pro Val Lys Gly Cys Thr Val Lys Tyr Thr
            115                 120                 125

Glu Ala Glu Ile Ala Ala Ala Cys Gln Thr Phe Leu Lys Leu Asn Asp
130                 135                 140

Tyr Leu Gln Val Glu Thr Ile Gln Ala Leu Glu Glu Leu Ala Val Arg
145                 150                 155                 160

Glu Lys Ala Asn Glu Asp Ala Val Pro Leu Cys Met Ala Glu Phe Pro
                165                 170                 175

Arg Ala Gly Val Gly Pro Ser Cys Asp Asp Glu Val Asp Leu Lys Ser
            180                 185                 190

Arg Ala Ala Tyr Asn Val Thr Leu Leu Asn Phe Met Asp Pro Gln Lys
            195                 200                 205

Met Pro Tyr Leu Lys Glu Glu Pro Tyr Phe Gly Met Gly Lys Met Ala
    210                 215                 220

Val Ser Trp His His Asp Glu Asn Leu Val Asp Arg Ser Ala Val Ala
225                 230                 235                 240
```

```
Val Tyr Ser Tyr Ser Cys Glu Gly Ser Glu Asp Glu Ser Glu Asp Glu
                245                 250                 255

Ser Ser Phe Glu Gly Arg Asp Pro Asp Thr Trp His Val Gly Phe Lys
            260                 265                 270

Ile Ser Trp Asp Ile Glu Thr Pro Gly Leu Thr Ile Pro Leu His Gln
        275                 280                 285

Gly Asp Cys Tyr Phe Met Leu Asp Asp Leu Asn Ala Thr His Gln His
    290                 295                 300

Cys Val Leu Ala Gly Ser Gln Pro Arg Phe Ser Ser Thr His Arg Val
305                 310                 315                 320

Ala Glu Cys Ser Thr Gly Thr Leu Asp Tyr Ile Leu Glu Arg Cys Gln
                325                 330                 335

Leu Ala Leu Gln Asn Val Leu Asn Asp Ser Asp Gly Asp Val Ser
            340                 345                 350

Leu Lys Ser Phe Asp Pro Ala Val Leu Lys Gln Gly Glu Glu Ile His
        355                 360                 365

Asn Glu Val Glu Phe Glu Trp Leu Arg Gln Phe Trp Phe Gln Gly Ser
    370                 375                 380

Arg Tyr Lys Leu Cys Thr Asp Trp Trp Cys Glu Pro Met Thr His Leu
385                 390                 395                 400

Glu Gly Leu Trp Lys Lys Met Glu Ser Met Thr Asn Ala Val Leu Arg
                405                 410                 415

Glu Val Lys Arg Glu Gly Leu Pro Val Glu Gln Arg Ser Glu Ile Leu
            420                 425                 430

Ser Ala Ile Leu Val Pro Leu Thr Val Arg Gln Asn Leu Arg Lys Glu
        435                 440                 445

Trp His Ala Arg Cys Gln Ser Arg Val Val Arg Thr Leu Pro Val Gln
    450                 455                 460

Gln Lys Pro Asp Cys Arg Pro Tyr Trp Glu Lys Asp Pro Ser Met
465                 470                 475                 480

Pro Leu Pro Phe Asp Leu Thr Asp Val Val Ser Glu Leu Arg Gly Gln
                485                 490                 495

Leu Leu Glu Ala Arg Ser
            500

<210> SEQ ID NO 9
<211> LENGTH: 502
<212> TYPE: PRT
<213> ORGANISM: Rattus norvegicus
<220> FEATURE:
<221> NAME/KEY: SITE
<222> LOCATION: (78)..(118)
<223> OTHER INFORMATION: Nucleotide-recognition lid
<220> FEATURE:
<221> NAME/KEY: SITE
<222> LOCATION: (119)..(320)
<223> OTHER INFORMATION: catalytic core

<400> SEQUENCE: 9

Met Lys Arg Val Gln Thr Ala Glu Glu Arg Glu Arg Glu Ala Lys Lys
1               5                   10                  15

Leu Arg Leu Leu Glu Glu Leu Glu Asp Thr Trp Leu Pro Tyr Leu Thr
            20                  25                  30

Pro Lys Asp Asp Glu Phe Tyr Gln Gln Trp Gln Leu Lys Tyr Pro Lys
        35                  40                  45

Leu Val Phe Arg Glu Ala Gly Ser Ile Pro Glu Glu Leu His Lys Glu
    50                  55                  60
```

-continued

```
Val Pro Glu Ala Phe Leu Thr Leu His Lys His Gly Cys Leu Phe Arg
 65                  70                  75                  80

Asp Leu Val Arg Ile Gln Gly Lys Asp Val Leu Thr Pro Val Ser Arg
                 85                  90                  95

Ile Leu Ile Gly Asp Pro Gly Cys Thr Tyr Lys Tyr Leu Asn Thr Arg
            100                 105                 110

Leu Phe Thr Val Pro Trp Pro Val Lys Gly Cys Thr Ile Asn Tyr Thr
        115                 120                 125

Glu Ala Glu Ile Ala Ala Cys Gln Thr Phe Leu Lys Leu Asn Asp
130                 135                 140

Tyr Leu Gln Val Glu Thr Ile Gln Ala Leu Glu Leu Ala Ile Lys
145                 150                 155                 160

Glu Lys Ala Asn Glu Asp Ala Val Pro Leu Cys Met Ala Glu Phe Pro
                165                 170                 175

Arg Ala Gly Val Gly Pro Ser Cys Asp Asp Glu Val Asp Leu Lys Ser
            180                 185                 190

Arg Ala Ala Tyr Asn Val Thr Leu Leu Asn Phe Met Asp Pro Gln Lys
        195                 200                 205

Met Pro Tyr Leu Lys Glu Glu Pro Tyr Phe Gly Met Gly Lys Met Ala
210                 215                 220

Val Ser Trp His His Asp Glu Asn Leu Val Asp Arg Ser Ala Val Ala
225                 230                 235                 240

Val Tyr Ser Tyr Ser Cys Glu Gly Ser Glu Asp Ser Asp Asp Glu
                245                 250                 255

Ser Ser Phe Glu Gly Arg Asp Pro Asp Thr Trp His Val Gly Phe Lys
            260                 265                 270

Ile Ser Trp Asp Ile Glu Thr Pro Gly Leu Thr Ile Pro Leu His Gln
        275                 280                 285

Gly Asp Cys Tyr Phe Met Leu Asp Asp Leu Asn Ala Thr His Gln His
290                 295                 300

Cys Val Leu Ala Gly Ser Gln Pro Arg Phe Ser Ser Thr His Arg Val
305                 310                 315                 320

Ala Glu Cys Ser Thr Gly Thr Leu Asp Tyr Ile Leu Gln Arg Cys Gln
                325                 330                 335

Leu Ala Leu Gln Asn Val Leu Asn Asp Ser Asp Asn Gly Asp Val Ser
            340                 345                 350

Leu Lys Ser Phe Glu Pro Ala Val Leu Lys Gln Gly Glu Glu Ile His
        355                 360                 365

Asn Glu Val Glu Phe Glu Trp Leu Arg Gln Phe Trp Phe Gln Gly Asn
370                 375                 380

Arg Tyr Lys Ile Cys Thr Asp Trp Cys Glu Pro Met Thr Gln Leu
385                 390                 395                 400

Glu Gly Leu Trp Lys Lys Met Glu Ser Val Thr Asn Ala Val Leu Arg
                405                 410                 415

Glu Val Lys Arg Glu Gly Leu Ser Val Glu Gln Arg Ser Glu Ile Leu
            420                 425                 430

Ser Ala Val Leu Ile Pro Leu Thr Met Arg Gln Asn Leu Arg Lys Glu
        435                 440                 445

Trp His Ala Arg Cys Gln Ala Arg Val Val Arg Thr Leu Pro Ala Gln
450                 455                 460

Gln Lys Pro Asp Cys Arg Pro Tyr Trp Glu Lys Asp Asp Pro Ser Met
465                 470                 475                 480

Pro Leu Pro Phe Asp Leu Thr Asp Val Val Ser Glu Ile Arg Ser Gln
                485                 490                 495
```

-continued

```
Leu Leu Glu Ala Arg Ser
            500

<210> SEQ ID NO 10
<211> LENGTH: 579
<212> TYPE: PRT
<213> ORGANISM: Danio rerio
<220> FEATURE:
<221> NAME/KEY: SITE
<222> LOCATION: (88)..(129)
<223> OTHER INFORMATION: Nucleotide-recognition lid
<220> FEATURE:
<221> NAME/KEY: SITE
<222> LOCATION: (130)..(399)
<223> OTHER INFORMATION: catalytic core

<400> SEQUENCE: 10

Met Lys Pro Arg Gln Arg Lys Gln Tyr Phe Arg Asn Met Lys Arg Ser
1               5                   10                  15

Asp Asp Ser Glu Arg Glu Lys Arg Arg Lys Arg Arg Leu Leu Gln
            20                  25                  30

Glu Leu Gly Glu Gln Arg Ile Pro Tyr Leu Ser Pro Thr Asp Pro Gly
        35                  40                  45

Phe Gln Asp Leu Trp Asp Ser Ser Tyr Ala Gly Leu Ala Leu Arg Gln
    50                  55                  60

Ser Gly Thr Leu Pro Glu Gly Leu His Glu Lys Val Gln Ser Ala Leu
65                  70                  75                  80

Leu Thr Leu Gln Arg His Gly Cys Leu Leu Arg Asp Leu Val Arg Val
                85                  90                  95

Arg Asp Arg Asp Val Phe Thr Ala Val Ser Arg Ala Leu Val Gly Gln
            100                 105                 110

Pro Gly Tyr Thr Tyr Arg Tyr Leu Asp Thr Arg Leu Phe Thr Ile Pro
        115                 120                 125

Trp His Cys Glu Gly Glu Gly Gln Lys Asp Glu Lys Gly Lys Pro
    130                 135                 140

Cys Cys Asp Ser Asp Leu Arg Asp Ala Cys Lys Ala Leu Trp Glu Leu
145                 150                 155                 160

Asn Gln Phe Phe Cys Ser Asp Val Lys Gln Gln Thr Asn Ala Arg Gly
                165                 170                 175

Val Lys Arg Thr Arg Ser Asp Thr Glu Asn Ser Glu Asp Ala Pro Gly
            180                 185                 190

Glu Gly Met Cys Glu Glu Glu Ser Val Lys Asp Arg Leu Val Glu Glu
        195                 200                 205

Lys Thr Ile Glu Glu Glu Glu Asp Ser Gly Gln Gly Cys Ser His
    210                 215                 220

Ser Ser Pro Pro Ser Ser Thr Pro Ala Ala Gln Ala Ser Leu Val
225                 230                 235                 240

Gln Phe Asn Val Thr Leu Ile Asn Tyr Met Asn Pro Ala Ala Met Thr
                245                 250                 255

Gln Leu Lys Glu Glu Pro Tyr Tyr Gly Met Gly Lys Met Ala Val Gly
            260                 265                 270

Trp His His Asp Glu Asn Leu Val Pro Leu Ser Pro Val Ala Val Tyr
        275                 280                 285

Ser Tyr Ser Cys Pro Ala Glu Pro Lys Asn Glu Gly Val Thr Glu Lys
    290                 295                 300

Asp Gly Glu Gly Lys Ser Lys Gly Lys Glu Arg Glu Ala Lys Gly Glu
305                 310                 315                 320
```

```
Gly Thr Ser Thr Glu Glu Val Lys Lys Glu Gly Ala Ser Val Lys
            325                 330                 335

Glu Asp Val Glu Lys Glu Lys Thr Cys Trp Arg Val Gly Leu Lys Val
        340                 345                 350

Ala Trp Asp Ile His Thr Pro Gly Leu Ala Leu Pro Leu Gln Ser Gly
        355                 360                 365

Asp Cys Tyr Tyr Met Thr Asp Leu Asn Arg Thr His Gln His Cys
        370                 375                 380

Val Leu Ala Gly Asp Thr Ala Arg Phe Ser Ser Thr His Arg Val Ala
385                 390                 395                 400

Gln Cys Cys Thr Gly Thr Leu Asp Tyr Ile Gln Lys Arg Cys Ser Glu
        405                 410                 415

Ala Leu Glu Asn Leu His Ser Asp Pro Glu Lys Asn Ala Lys Ser Leu
        420                 425                 430

Ile Ser Leu Leu Pro Ser Ile Leu Gln Arg Ile Glu Asp Ile His Asn
        435                 440                 445

Glu Val Glu Phe Glu Trp Leu Arg Gln Tyr Trp Phe Gln Gly Arg Arg
        450                 455                 460

Tyr Ala Arg Phe Cys Ser Trp Trp Thr Lys Pro Met Glu Gln Met Glu
465                 470                 475                 480

Lys Asp Trp Lys Glu Met Glu Arg Met Thr Gln Leu Leu Val Val
        485                 490                 495

Val Glu Asp Glu Ala Thr Ala Gln Glu Asn Arg Arg Glu Met Ala Asp
        500                 505                 510

Val Leu Leu Asn Ala Leu Thr Asp Arg Gln Gln His Arg Gln Thr Trp
        515                 520                 525

Arg Asp Arg Cys Gln Ser Ser Leu Ala Gln Thr Leu Pro Pro Glu Glu
        530                 535                 540

Ala Pro Val Asp Arg Pro Tyr Trp Ser Asn Asp Pro Asp Met Pro
545                 550                 555                 560

Leu Pro Phe Asp Leu Ser Asp Ile Ile Asn Arg Val Glu Ser Leu Leu
        565                 570                 575

Trp Arg Met

<210> SEQ ID NO 11
<211> LENGTH: 498
<212> TYPE: PRT
<213> ORGANISM: Xenopus tropicalis
<220> FEATURE:
<221> NAME/KEY: SITE
<222> LOCATION: (77)..(117)
<223> OTHER INFORMATION: Nucleotide-recognition lid
<220> FEATURE:
<221> NAME/KEY: SITE
<222> LOCATION: (118)..(316)
<223> OTHER INFORMATION: catalytic core

<400> SEQUENCE: 11

Met Lys Arg Gly Val Leu Cys Glu Glu Glu Lys Gly Ala Lys Lys Gln
1               5                   10                  15

Lys Leu Leu Asp Gln Ile Gly Asp Gly His Leu Pro Tyr Leu Ser Pro
            20                  25                  30

Lys Asp Asp Thr Phe Tyr Asp Leu Trp Arg Thr Cys Tyr Ser Lys Leu
        35                  40                  45

Thr Leu Leu Gln Ala Lys His Ile Asn Ala Asp Leu His His Thr Val
    50                  55                  60

Gln Asn Ala Phe Leu Ser Leu Leu Asp Asn Gly Cys Leu Phe Gln Asp
65              70                  75                  80
```

```
Leu Val Arg Leu Lys Gly Lys Asp Ile Leu Thr Pro Val Ser Arg Ile
                85                  90                  95

Leu Ile Gly Arg Pro Gly Tyr Thr Tyr Lys Tyr Leu Asn Thr Arg Leu
            100                 105                 110

Phe Ala Val Pro Trp Ile Asn Asp Glu Leu Asn Thr Gln Tyr Cys Thr
            115                 120                 125

Arg Asn Leu Leu Asp Thr Tyr Lys Ala Phe Ser Asp Leu Asn Lys Phe
        130                 135                 140

Leu Tyr Ser Gln Thr Val Asn Glu Leu Gln Lys Leu Arg Lys Ala His
145                 150                 155                 160

Lys Asn Asp Cys Phe Gln His Phe Asp Tyr Lys Glu Gln Val Lys Ser
                165                 170                 175

Asp Lys Arg Pro Cys Thr Leu Asn Asn Glu Asn Lys Glu Leu His Ser
            180                 185                 190

Leu Glu Pro Phe Asn Val Thr Leu Ile Asn Tyr Met Asp Pro Arg Asp
            195                 200                 205

Met Pro Cys Leu Lys Glu Glu Pro Tyr Phe Gly Met Gly Lys Met Ala
    210                 215                 220

Val Ser Trp His His Asp Glu Asn Leu Val Glu Gln Ser Thr Val Ala
225                 230                 235                 240

Val Tyr Asn Phe Ser Tyr Gln Glu Ser Ala His Asp Ile Asn Gly Asp
                245                 250                 255

Asp Lys Asp Pro Ala Thr Trp Asn Val Gly Leu Lys Ile Ala Trp Asp
            260                 265                 270

Ile Glu Thr Pro Gly Leu Cys Ile Pro Leu Asn Thr Gly Asp Cys Tyr
            275                 280                 285

Leu Met Leu Asp Asp Leu Asn Lys Thr His Gln His Cys Val Ile Ala
    290                 295                 300

Gly Cys Gln Pro Arg Phe Ser Ser Thr His Arg Val Ala Glu Ser Ser
305                 310                 315                 320

Arg Asp Thr Phe Gln Tyr Ile Lys Ser Gln Cys Asn Ser Ala Leu Gln
                325                 330                 335

Asn Leu His Met Asp Pro Asp Thr Gly Ala Ala Ala Leu Lys Ser Leu
            340                 345                 350

Glu Pro Arg Val Leu Gly Gln Thr Glu Glu Ile His Asn Glu Val Glu
            355                 360                 365

Phe Glu Trp Leu Arg Gln Phe Trp Phe Gln Gly Lys Arg Tyr Asn Lys
    370                 375                 380

Cys Thr Thr Phe Trp Lys Glu Ala Met Thr Glu Leu Glu Asn His Trp
385                 390                 395                 400

Lys Gln Met Glu Thr Met Thr Ser Leu Val Leu Lys Ala Ile Glu Asn
                405                 410                 415

Glu Asn Leu Thr Val Asp Glu Lys Cys Asn Ile Leu Lys Asn Ile Leu
            420                 425                 430

Pro Cys Leu Val Glu Arg Gln Asn Leu Arg Gln Glu Trp Arg Glu Arg
            435                 440                 445

Cys Arg Ser Lys Leu Ala Lys Lys Leu Pro Pro Asp Gln Ala Pro Cys
    450                 455                 460

Cys Tyr Pro Tyr Trp Asn Asp Asn Lys Ser Met Pro Leu Ser Phe
465                 470                 475                 480

Asp Leu His Ser Ile Thr Phe Ala Leu Gln Asn Arg Leu Glu Thr Leu
                485                 490                 495

Glu Ala
```

<210> SEQ ID NO 12
<211> LENGTH: 286
<212> TYPE: PRT
<213> ORGANISM: Homo sapiens

<400> SEQUENCE: 12

Met Glu Glu Lys Arg Arg Ala Arg Val Gln Gly Ala Trp Ala Ala
1               5                   10                  15

Pro Val Lys Ser Gln Ala Ile Ala Gln Pro Ala Thr Thr Ala Lys Ser
                20                  25                  30

His Leu His Gln Lys Pro Gly Gln Thr Trp Lys Asn Lys Glu His His
            35                  40                  45

Leu Ser Asp Arg Glu Phe Val Phe Lys Glu Pro Gln Gln Val Val Arg
50                  55                  60

Arg Ala Pro Glu Pro Arg Val Ile Asp Arg Glu Gly Val Tyr Glu Ile
65                  70                  75                  80

Ser Leu Ser Pro Thr Gly Val Ser Arg Val Cys Leu Tyr Pro Gly Phe
                85                  90                  95

Val Asp Val Lys Glu Ala Asp Trp Ile Leu Glu Leu Cys Gln Asp
            100                 105                 110

Val Pro Trp Lys Gln Arg Thr Gly Ile Arg Glu Asp Ile Thr Tyr Gln
            115                 120                 125

Gln Pro Arg Leu Thr Ala Trp Tyr Gly Glu Leu Pro Tyr Thr Tyr Ser
130                 135                 140

Arg Ile Thr Met Glu Pro Asn Pro His Trp His Pro Val Leu Arg Thr
145                 150                 155                 160

Leu Lys Asn Arg Ile Glu Glu Asn Thr Gly His Thr Phe Asn Ser Leu
                165                 170                 175

Leu Cys Asn Leu Tyr Arg Asn Glu Lys Asp Ser Val Asp Trp His Ser
            180                 185                 190

Asp Asp Glu Pro Ser Leu Gly Arg Cys Pro Ile Ile Ala Ser Leu Ser
            195                 200                 205

Phe Gly Ala Thr Arg Thr Phe Glu Met Arg Lys Lys Pro Pro Pro Glu
210                 215                 220

Glu Asn Gly Asp Tyr Thr Tyr Val Glu Arg Val Lys Ile Pro Leu Asp
225                 230                 235                 240

His Gly Thr Leu Leu Ile Met Glu Gly Ala Thr Gln Ala Asp Trp Gln
                245                 250                 255

His Arg Val Pro Lys Glu Tyr His Ser Arg Glu Pro Arg Val Asn Leu
            260                 265                 270

Thr Phe Arg Thr Val Tyr Pro Asp Pro Arg Gly Ala Pro Trp
            275                 280                 285

<210> SEQ ID NO 13
<211> LENGTH: 15
<212> TYPE: DNA
<213> ORGANISM: artificial sequence
<220> FEATURE:
<223> OTHER INFORMATION: oligonucleotide
<220> FEATURE:
<221> NAME/KEY: modified_base
<222> LOCATION: (3)..(3)
<223> OTHER INFORMATION: methylated base
<220> FEATURE:
<221> NAME/KEY: misc_feature
<222> LOCATION: (3)..(3)
<223> OTHER INFORMATION: n is a, c, g, or t

<400> SEQUENCE: 13

```
ttnttttttt ttttt                                                15

<210> SEQ ID NO 14
<211> LENGTH: 24
<212> TYPE: DNA
<213> ORGANISM: artificial sequence
<220> FEATURE:
<223> OTHER INFORMATION: oligonucleotide

<400> SEQUENCE: 14
gctagcatga agcgcgtcca gacc                                      24

<210> SEQ ID NO 15
<211> LENGTH: 27
<212> TYPE: DNA
<213> ORGANISM: artificial sequence
<220> FEATURE:
<223> OTHER INFORMATION: oligonucleotide

<400> SEQUENCE: 15
gaattcctag gatcttgctt ccagcag                                   27
```

METHOD FOR ASSAYING FTO (2-OXOGLUTARATE DEPENDENT OXYGENASE) ACTIVITY

CROSS-REFERENCE TO RELATED APPLICATIONS

This application is the U.S. national stage filing under 35 U.S.C. §371 of international application PCT/GB2008/002119, filed Jun. 20, 2008, which claims priority from Great Britain Patent Application 0711955.5, filed Jun. 20, 2007, and Great Britain Patent Application 0721944.7, filed Nov. 8, 2007.

FIELD OF THE INVENTION

The present invention relates to assays for monitoring activity of the FTO protein and, in particular, to assays for identifying inhibitors, activators and substrates of the FTO protein. The present invention also relates to the treatment or prevention of weight gain, weight loss and disorders associated with weight gain and weight loss.

BACKGROUND TO THE INVENTION

Obesity correlates with an increased risk of a range of diseases including some types of cancer, heart disease and type two diabetes. Recently it has been reported that the presence of specific alleles in the FTO gene, located on human chromosome 16, correlates with obesity and type two diabetes. Specifically, sufferers of type two diabetes were found to have an increased likelihood of a particular FTO variant (rs9939609 A allele) which correlates with an increased body weight (Frayling et al. Science (2007) 316: 889-894). Subsequent analyses involving more than 39,000 individuals revealed that the FTO allele was associated with body weight. Individuals carrying one copy of the FTO variant associated with type two diabetes had a 30% increased risk of being obese compared to an individual with no copies of that version and were on average more than 1.2 kg heavier than individuals with no copies of the disease-associated variant. Individuals with two copies of the variant (about 16% of those analyzed) had a 70% increased risk of being obese and on average weighed 3 kg more than individuals with no copies of the disease-associated variant. This study is important, as no previous work has identified a risk allele for obesity that is so prevalent. Further studies show similar results (Dina et al. Nat Genet (2007) 39: 724-726; Scott et al. Science (2007) 316: 1341-1345).

The mouse ortholog of FTO, Fatso (Fto), is a gene that is deleted in the fused toes mouse mutant (Peters et al. Mann Genome (2002) 13: 186-188; van der Hoeven et al. Development (1994) 120: 1601-2607, Grotewold & Ruther, Dev Biol (2002) 251: 129-141; Anselme et al. Dev Biol (2007) 304: 208-220). For clarity, subsequent reference to FTO includes human FTO, non-human homologues and/or any of their clinically observed variations.

Although FTO sequence variation is linked to obesity, the function of its protein product at the biochemical, cellular and physiological levels has not been reported.

Knowledge about FTO structure and its biochemical, cellular and physiological roles is needed to enable the correlation between FTO and obesity to be exploited for the treatment of diseases associated with weight gain, such as diabetes, cardiovascular disease, cancer, osteoporosis and hypertenstion.

The 2-oxoglutarate (2-OG) and ferrous iron dependent oxygenases are a superfamily of enzymes that catalyse a wide range of reactions including hydroxylations, desaturations and oxidative ring closures (Hausinger (2004), Crit. Rev. Biochem. Mol. Biol. 39, 21-68; Ryle & Hausinger (2002) Curr. Opin. Chem. Biol. 6, 193-201; and Schofield et al. (1999) Journal of Inorganic Biochemistry 74, 49-49). Substrate oxidation is coupled to conversion of 2-OG to succinate and carbon dioxide. At least in some cases, binding of oxygen is followed by the oxidative decarboxylation of 2-OG to give succinate, $CO_2$ and a ferryl species $[Fe(IV)=O]$ at the iron centre. This highly reactive intermediate can then oxidize an unactivated C—H bond in the prime substrate, e.g. the oxidation of prolyl or asparaginyl residues in human proteins, or effect other oxidative reactions such as oxidation of methyl groups on N-methylated versions of proteins or nucleic acids. Evidence for intermediates comes from substrate-analogue studies, model compounds and spectroscopic analyses.

The sequential binding of co-substrate and prime substrate, which is necessary to trigger oxygen binding, is probably important in limiting the generation of reactive oxidizing species in the absence of prime substrate. The generation of such species in a prime-substrate-uncoupled manner can inactivate 2-OG and the related oxygenases through self-oxidation, which sometimes leads to fragmentation. Typically, the uncoupled turnover of 2-OG occurs at approximately 5% of the rate of its coupled turnover in the presence of saturating concentrations of prime substrate, although it can also occur at a lower or higher rate.

Several 2-OG-dependent oxygenases, including procollagen prolyl hydroxylase, the hypoxia inducible factor prolyl hydroxylases, and anthocyanidin synthase, have a requirement for ascorbate for full catalytic activity. Although ascorbate might stimulate activity by reducing $Fe^{3+}$, or other high valent forms of iron, to $Fe^{2+}$ (either free in solution or at the active site), the stimulation of oxygenase activity by ascorbate might occur by other mechanisms, for instance, by promoting completion of uncoupled cycles. For uncoupled reaction cycles that are catalysed by procollagen prolyl hydroxylase in the absence of prime substrate, the oxidation of 2-OG to succinate has been shown to be stoichiometrically coupled to ascorbate.

Furthermore, the activity of ascorbate has been shown to stimulate the activity of 2-OG oxygenases in cells (e.g. in work on the hypoxia inducible factor (HIF) prolyl hydroxylase) and lack of ascorbate in the human diet leads to the disease scurvy due to impaired activity of the procollagen prolyl hydroxylase.

Studies with several enzymes have shown that certain substrate analogues and mutants can also stimulate uncoupled 2-OG turnover. It is also known in the literature that reducing agents other than ascorbate itself can act as reducing agents in the uncoupled turnover reaction, including derivatives of ascorbate (Zhang et al. (1995) Biochem. J. 307 (Pt 1), 77-85 and Myllyla et al. (1978) Biochem. Biophys. Res. Commun. 83, 441-8).

A number of 2-OG oxygenases are of current therapeutic interest including the transcription factor hydroxylases, e.g. the hypoxia inducible factor prolyl and asparaginyl hydroxylases, methylated nucleic acid demethylases, methylated lysyl demethylases, procollagen prolyl and lysyl hydroxylases, phytanoyl CoA hydroxylase, Mina53, NO66 and arginyl hydroxylases such as phosphatidyl serine receptor (Jmjd6). The methyl lysyl demethylases may use methylated histones as preferred substrates and may use any of all the tri, di, or mono-methylated lysine residues as preferred substrates.

Methylation of nucleic acid and nucleic acid associated acid proteins, including histones, is a known mechanism for epigenetic inheritance. Methylation of nucleic acids can also affect gene activity and expression.

SUMMARY OF THE INVENTION

The present inventors have identified FTO as a 2-oxoglutarate (2-OG) dependent oxygenase and have demonstrated for the first time that FTO is a 2-OG dependent oxygenase. The present inventors have successfully purified recombinant FTO and demonstrated that the purified recombinant FTO functions as a 2-OG dependent oxygenase and can be inhibited by known 2-OG oxygenase inhibitors.

Accordingly, the present invention provides a method for assaying FTO activity, the method comprising monitoring oxygenase activity of a FTO polypeptide.

In a method of the invention oxygen and/or a 2-oxoacid, such as 2-OG may be used as a co-substrate and/or iron may be used as a co-factor. The assay for oxygenase activity may be monitored in the presence of a reducing agent, such as ascorbate, or an analogue thereof, a thiol or a phosphine. In one embodiment, FTO oxygenase activity is measured in the presence of a substrate, such as a peptide or nucleic acid substrate.

The FTO polypeptide used in a method of the invention may be a recombinant polypeptide. In one embodiment, the FTO polypeptide comprises: the amino acid sequence of SEQ ID NO: 1; or an amino acid sequence having at least 40% identity to the amino acid sequence of SEQ ID NO: 1 over its entire length. The amino acid having at least 40% identity to the amino acid sequence of SEQ ID NO: 1 over its entire length may be an amino acid sequence as shown in any one of SEQ ID Nos: 2 to 11. Alternatively, the acid sequence having at least 40% identity to the amino acid sequence of SEQ ID NO: 1 over its entire length may be a naturally occurring variant of human FTO or a homologue of FTO from a species other than human.

In one preferred embodiment, the invention provides a method comprising: contacting a FTO polypeptide with a test agent; monitoring for oxygenase activity in the presence of the test agent; and determining whether the test agent is an inhibitor or activator of FTO activity.

The test agent may be a known inhibitor of a 2-OG oxygenase other than FTO, or an analogue or variant of such an inhibitor.

The 2-OG oxygenase other than FTO may be, for example, a prolyl, lysyl, arginyl or asparaginyl demethylase, procollagen prolyl or lysyl hydroxylases, hypoxia inducible factor prolyl hydroxylase, methylated lysyl demethylase (including histone demethylases), asparaginyl hydroxylase, phosphatidyl serine receptor (Jmjd6), AlkB or human AlkB homologues and/or gibberellin C-20 oxidase. The known 2-OG inhibitor may be an N-oxalyl amino acid such as N-oxalylglycine or a derivative thereof, a glycine or alanine derivative, a 2-oxoacid analogue, a flavonoid or flavonoid derivative such as genistein.

In a method of the invention for identifying an inhibitor or activator of FTO, the test agent may compete with 2-OG or a FTO substrate at the FTO active site and/or bind to the metal at the FTO active site. The test agent may, for example, comprise a metal ion.

In one embodiment the test agent is a reducing agent, which may be a reported activator of a 2-OG oxygenase other than FTO. For example, the test agent may be ascorbate or an analogue of ascorbate or a reducing agent of the thiol, such as a member of the dithiothreitol or phosphine chemical families.

The substrate of the FTO polypeptide used in a method of the invention may be a nucleic acid, nucleic acid derivative or analogue. For example, the substrate may be a methylated nucleic acid. The methylated nucleic acid may be associated with a gene involved in weight modulation, such as the agouti gene or the neuropeptide Y gene, the leptin gene, the proopiomelanocortin gene, the orexin gene, the galanin gene, the PYY gene, the cholecystokinin gene, the glucagon-related peptide-1 gene or the insulin gene.

In one embodiment, the invention provides a method for identifying a substrate of FTO, the method comprising: contacting a FTO polypeptide with a test substrate; monitoring for oxygenase activity; and determining whether the test substrate is a substrate of FTO. The test substrate may be a human nucleic acid sequence, such as a nucleic acid sequence containing a 3-methylthymine base, a 1-methyladenine base or a 3-methylcytosine base. Alternatively, the test substrate may be a methylated protein or peptide. An FTO inhibitor may be used to enable identification of the FTO substrate by stabilizing the interaction between FTO and the substrate prior to identification of the substrate.

In one aspect, the invention provides a method of identifying an inhibitor or activator that selectively inhibits or activates FTO or that activates or inhibits an enzyme other than FTO but does not activate or inhibit FTO, the method comprising monitoring the activity of FTO in the presence of the test agent and repeating the method using an enzyme other than FTO and determining whether the test agent selectively inhibits or activates FTO or the other enzyme.

In one embodiment of the invention, the enzyme other than FTO is typically a 2-OG oxygenase, such as a hypoxia inducible factor hydroxylase, such as a prolyl, asparaginyl or lysyl hydroxylase, a collagen or procollagen prolyl hydroxylase, a nucleic acid demethylase such as an AlkB homologue, or a protein demethylase, such as a tri-, di- or mono-methyl lysine, arginine, asparagine or proline residue demethylase. The protein demethylase may hydroxylate a methylated histone or a fragment thereof.

In further embodiments, the invention provides:
  the use of an inhibitor or activator of 2-OG oxygenase activity to modulate FTO activity;
  a modulator of FTO oxygenase activity for use in a method of treating or preventing weight gain or weight loss or treating or preventing a disease associated with weight gain or weight loss;
  a method of treating or preventing weight gain or weight loss in an individual in need thereof, the method comprising administering to the individual a therapeutically effective amount of an inhibitor or activator of FTO oxygenase activity; and
  a method of treating or preventing a disease associated with weight gain or weight loss in an individual in need thereof, the method comprising administering to an individual a therapeutically effective amount of an inhibitor or activator of FTO oxygenase activity.

BRIEF DESCRIPTION OF THE FIGURES

Figure 1:
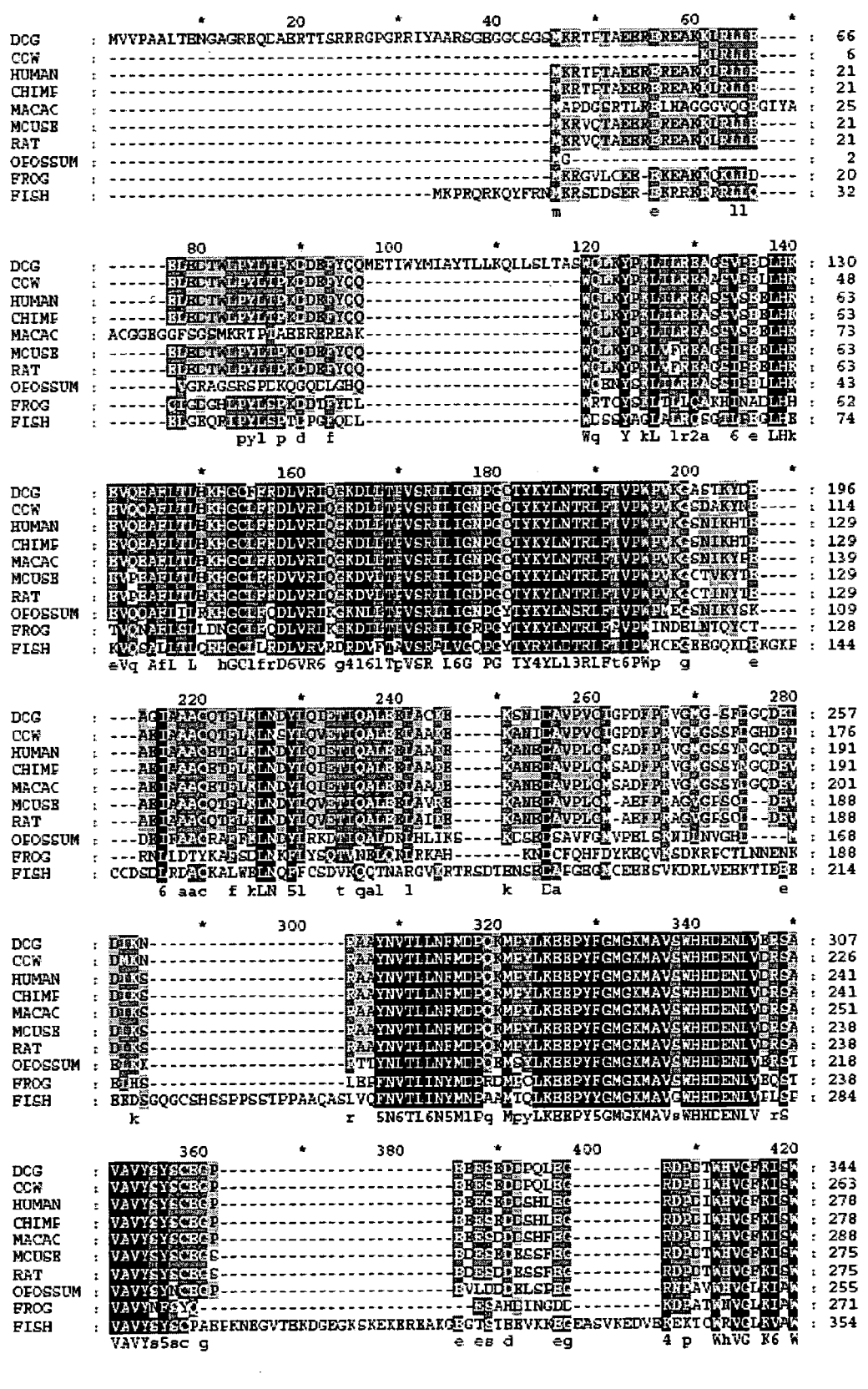
Figure 1:
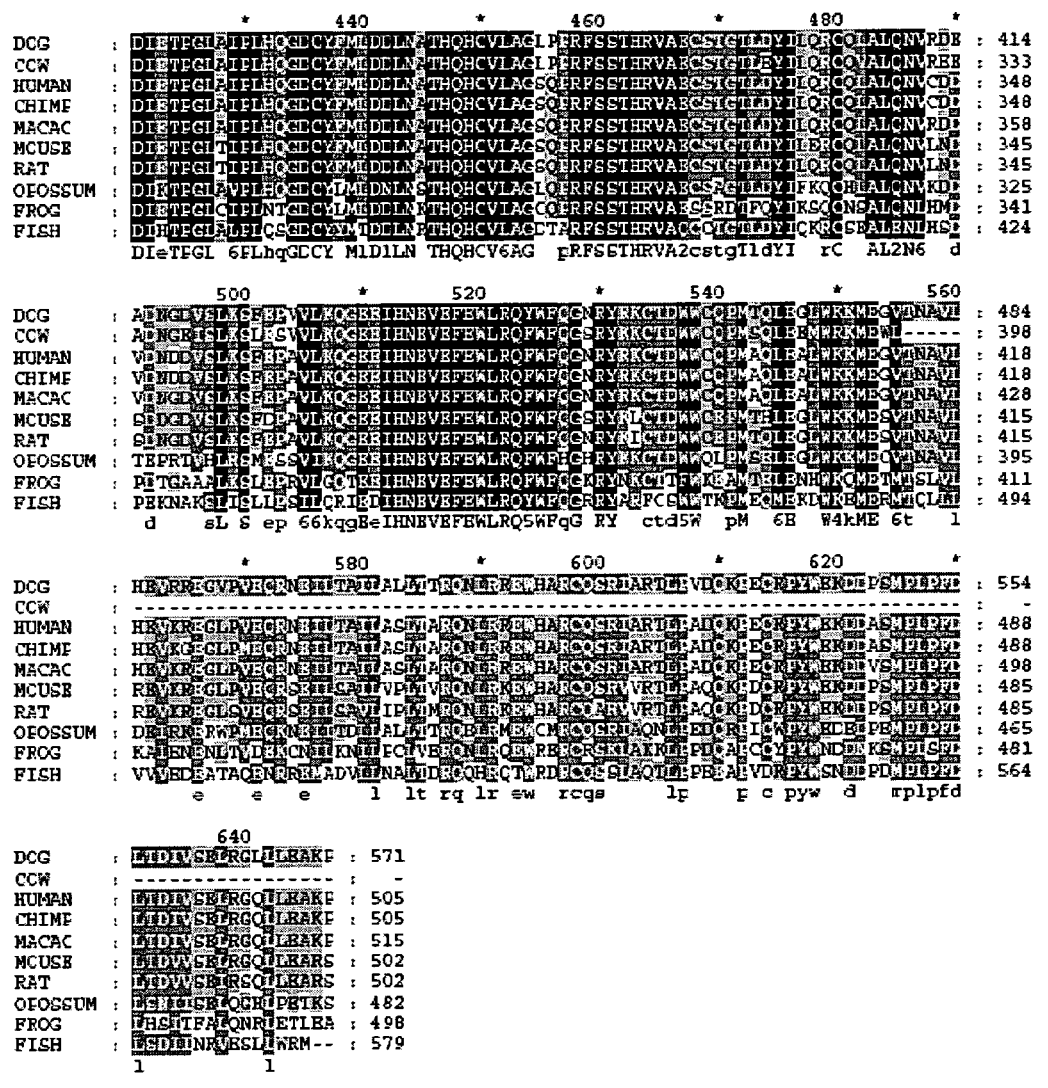

FIG. 1 shows a clustalW alignment of FTO homologue sequences. Human gi|122937263, chimp gi|114662524 (*99%), Macaque gi|109128525 (*93%), dog gi|73950384 (*91%), cow gi|119910109 (*88%), opossum gi|126296336 (*65%), mouse gi|18490097 (*87%), mouse2 gi|6753916

(*87%), rat gi|89337260 (*87%), fish gi|125821796 (*48%), frog gi|62859671 (*52%) [* indicates identity with human FTO].

Figure 2:
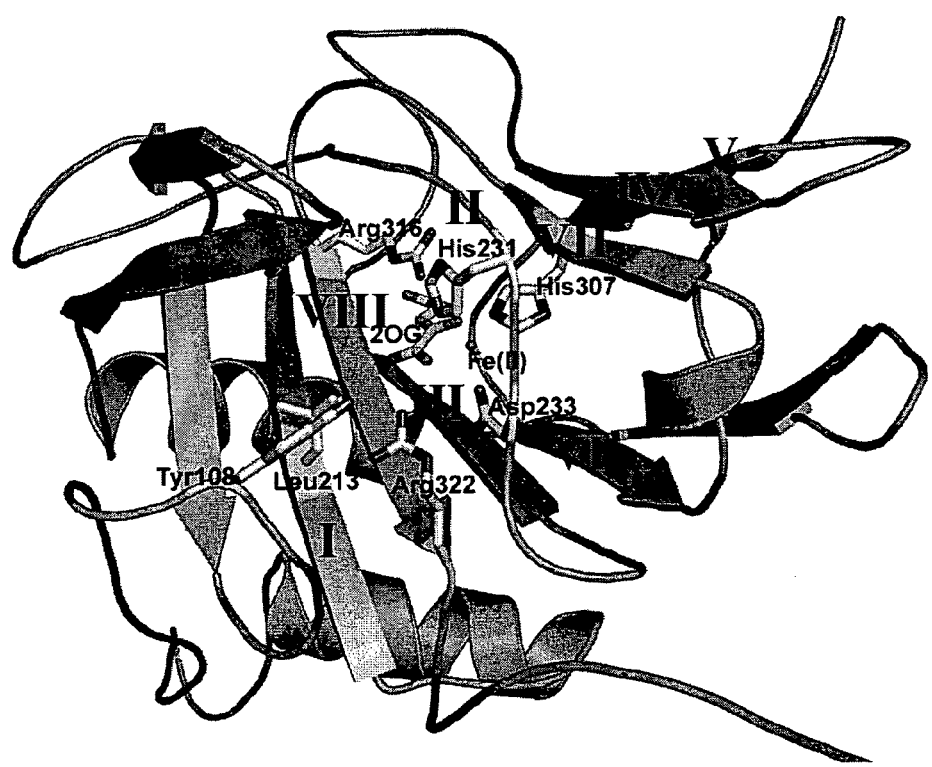
Figure 5:
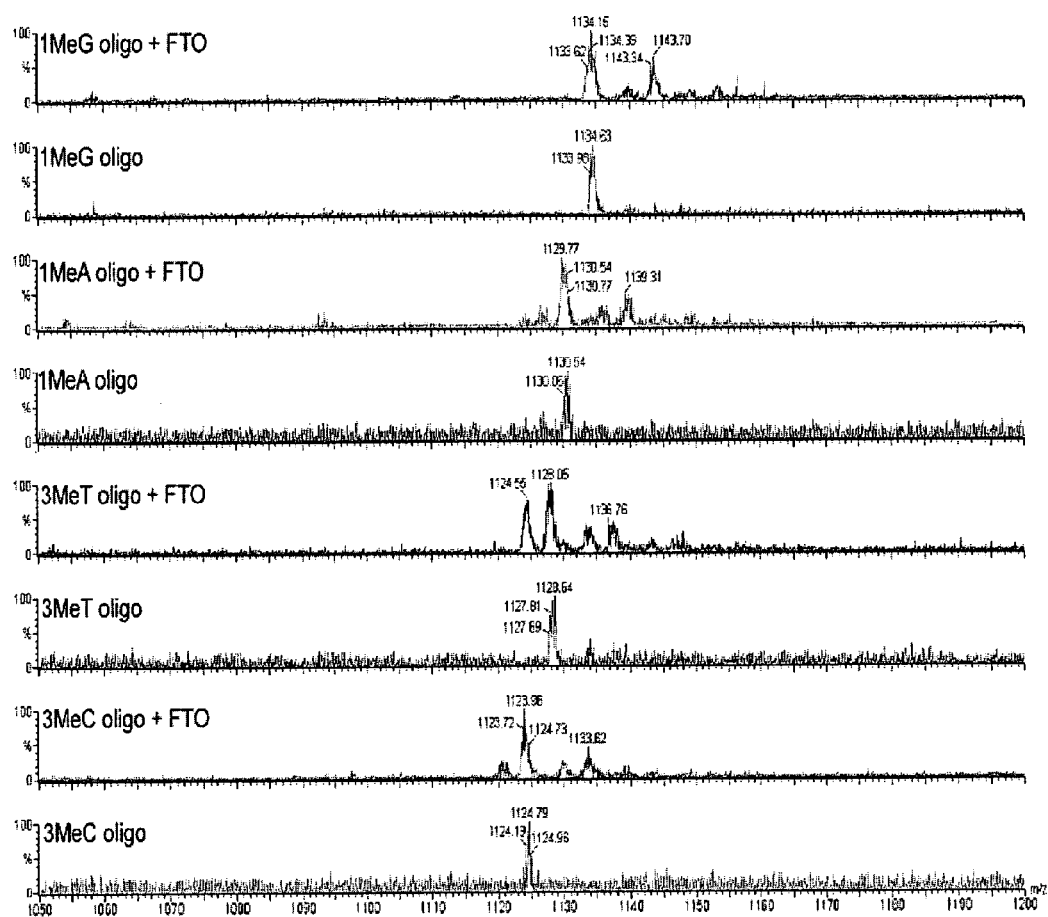

FIG. 2 is a homology model of FTO based on its sequence and secondary structure alignment with ABH3 (FIG. 5).

FIG. 3 shows the sequence and secondary structure alignment (secondary structure predicted for FTO) for FTO and ABH3. Roman numerals indicate the eight core DSBH strands. There is a C-terminal helical domain subsequent to the DSBH domain.

Figure 4:
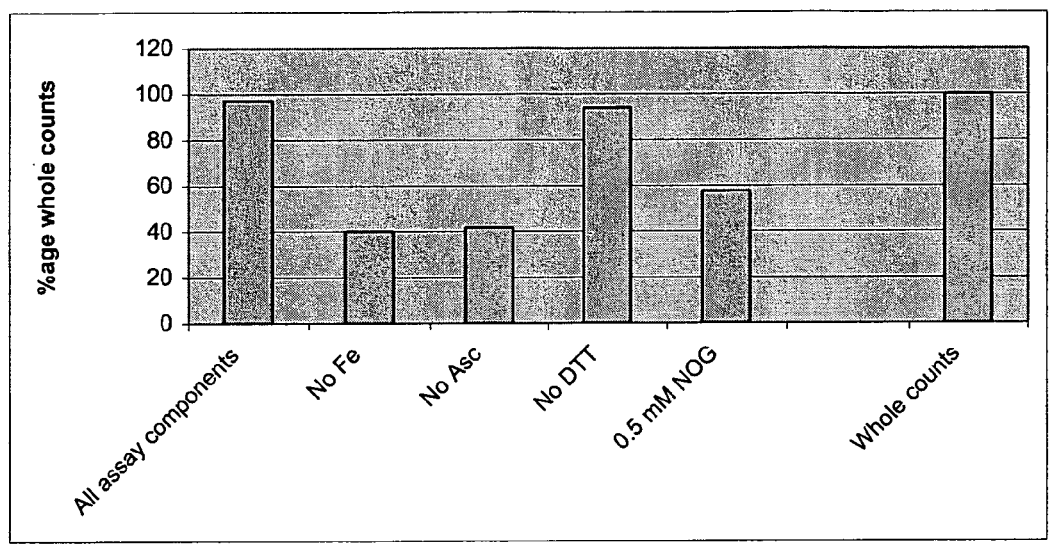

FIG. 4 shows the results of a 2-OG turnover assay for determining enzymatic activity of FTO. The assay was carried out using 11.5 μM FTO, 144 μM 20G, 16 μM $^{14}$C-20G, 80 μM $(NH_4)_2Fe(II) (SO_4)_2$, 4 μM ascorbate and 1 mM DTT and with one of $(NH_4)_2 Fe(II)(SO_4)_2$, ascorbate and DTT missing from the assay. The assay was also performed in the presence of N-oxalylglycine (NOG).

FIG. 5 shows the results of Mass Spectroscopy (MS) analyses for demethylation of oligonucleotides with recombinant FTO. The data shown is for TTX TTT TTT TTT TTT (T=thymine, X— methylated base) SEQ ID NO: 13 for the 4-charge state. +FTO=incubation with FTO with appropriate cofactors and cosubstrates. 3MeT=3-methyl thymine; 1MeA=1-methyl adenine; 3MeC=3-methylcytosine.

Figure 6:
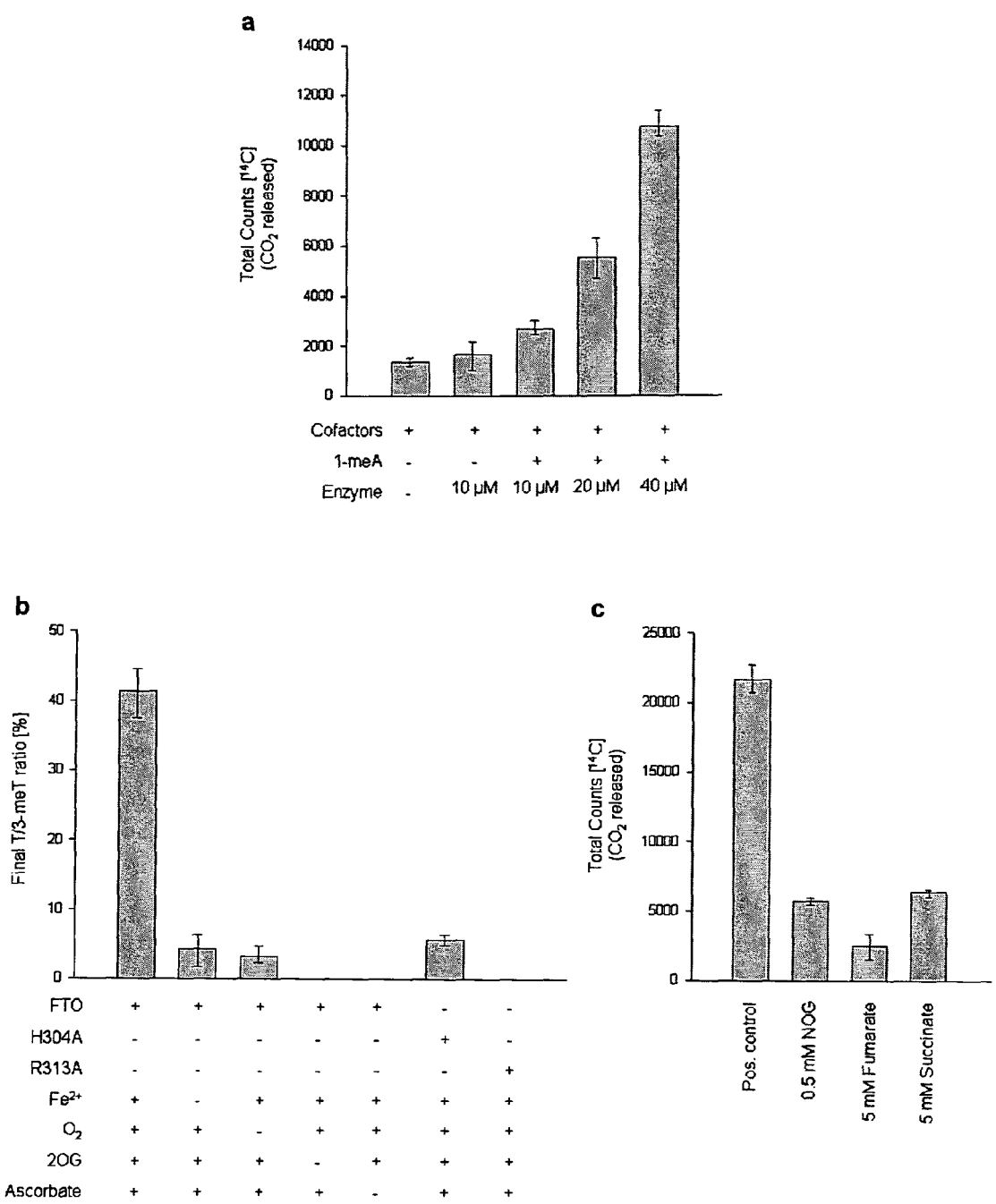

FIG. 6 shows the results of experiments testing the 2-OG-dependent DNA demethylase activity of FTO: (a) Demethylation of 1-meA is dependent on FTO in 2-OG decarboxylation assays; (b) Cofactor/cosubstrate dependence of FTO activity on a 3-meT substrate shown by LC-MS. Data shown represent ratios of thymine to 3-meT in ss-DNA. The oxygen control reaction was carried out in an atmosphere of <1% $O_2$; (c) Inhibition of FTO-catalyzed 1-meA.

Figure 7:
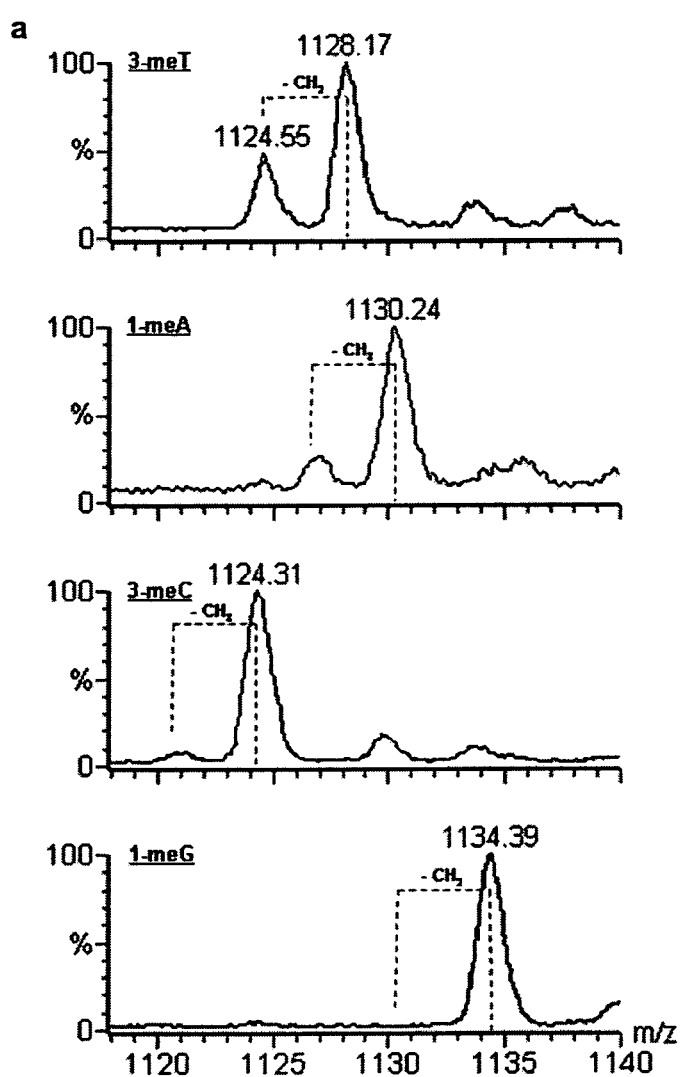
Figure 7:
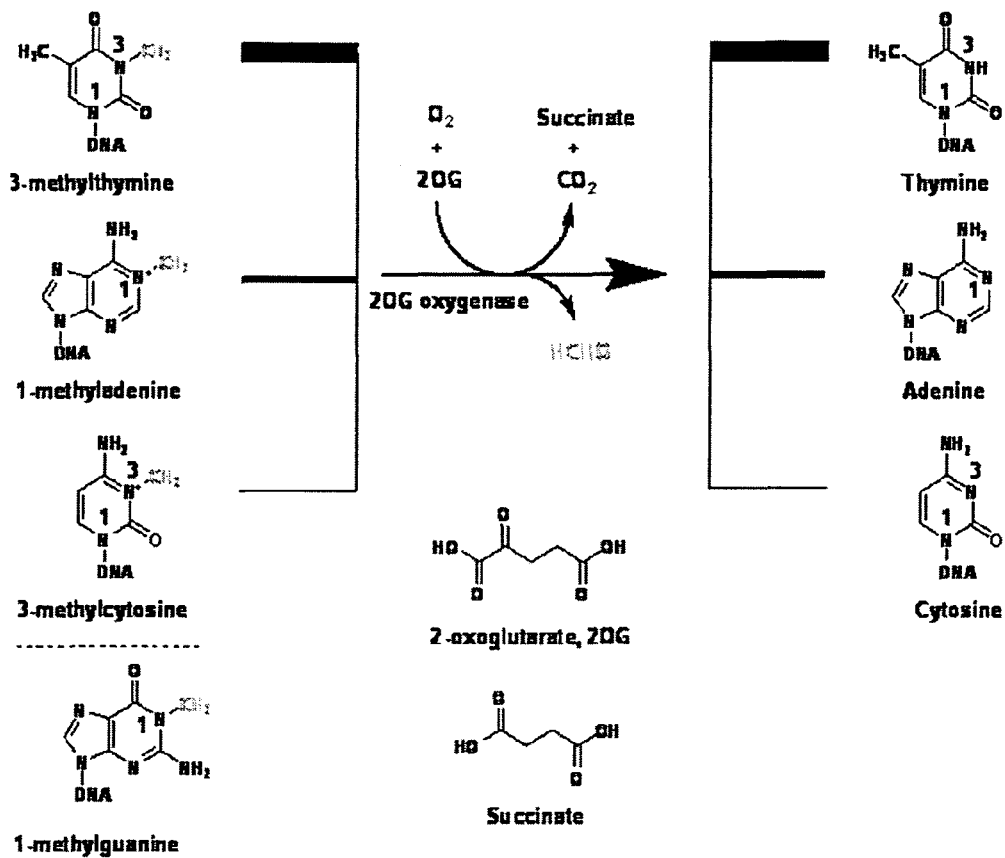
Figure 7:
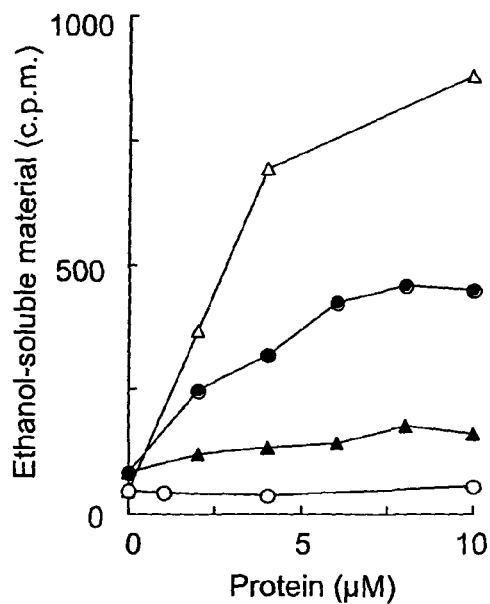

FIG. 7 shows: (a) the results of mass spectroscopy analyses for demethylation of single stranded DNA substrates by FTO. LC-MS data for the incubation of synthetic 15-mer of poly T, methylated at the 2-position, with FTO, cofactors and co-substrates; positions of expected peaks for demethylated substrates are indicated by dotted lines. Smaller peaks at higher masses than reactant peaks probably arise from $Na^+$ and $K^+$ adducts of the methylated oligonucleotides. m/z=mass-to-charge ratio, shown in units of Dalton; (b) Stoichiometry of the FTO reaction; (c) Release of formaldehyde from methylated poly(dA) and poly(dT). FTO and ABH3 were assayed for demethylase activity by incubation with CM-methylated poly(dA) or [$^{14}$C]-methylated poly(dT) (total c.p.m. 1000 or 800, respectively) at 37° C. for 15 minutes. Release of ethanol-soluble [$^{14}$C]-formaldehyde was monitored. FTO -○-, -●-; ABH3 -Δ-, -▲-. [$^{14}$C]-methylated poly(dA)-○-, -Δ-; [$^{14}$C]-methylated poly(dT)-●-, -▲-. In the absence of 2-OG, no significant activity was detected.

Figure 8:
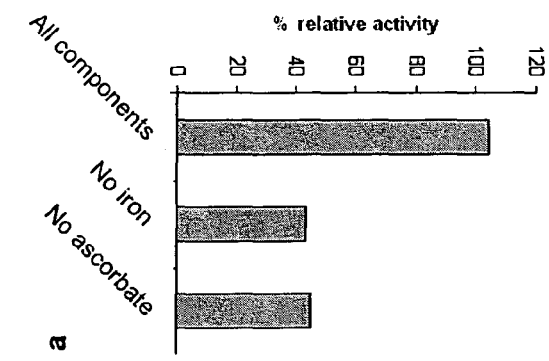
Figure 8:
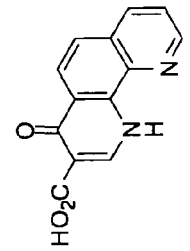
Figure 8:
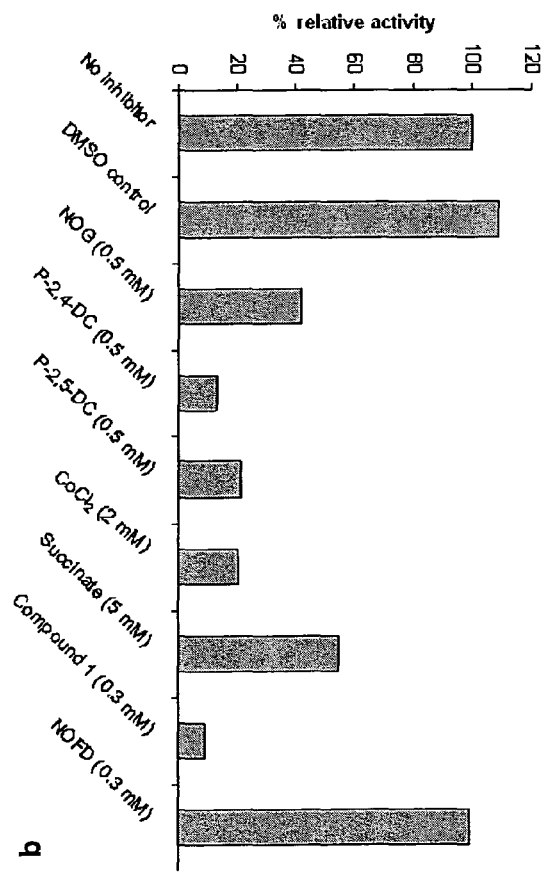
Figure 8:
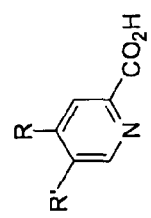
Figure 8:
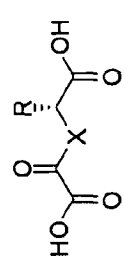

FIG. 8 shows the results of uncoupled 2-OG turnover experiments: (a) Assays used the 2-OG turnover method; no methylated DNA substrate was added. Experimental setup and procedure were as described in the Examples. Values shown are averages of two independent experiments, 100% corresponds to 130,000 counts of [$^{14}$C]—$CO_2$; (b) Reduction of uncoupled 2-OG turnover in the presence of inhibitors. DMSO=dimethylsulfoxide. Although N-oxalylglycine can chelate Fe(II), this does not fully account for its FTO inhibitory effect because N-oxalyl-D-phenylalanine (10), an inhibitor of a 2-OG dependent asparagine-hydroxylase, has similar Fe(II) chelating abilities to N-oxalylglycine but did not inhibit FTO activity. Values shown are averages of two independent experiments, 100% corresponds to 130,000 counts of [$^{14}$C]—$CO_2$; (c) Structures of inhibitors used. Compound 1 was previously identified as a potent 2-OG oxygenase inhibitor Franklin et al., 2001, Biochem J. 353:333 and synthesized using standard synthetic methodology (Banerji et al., 2005, Chem. Comm. 43:5438).

BRIEF DESCRIPTION OF THE SEQUENCES

SEQ ID NO: 1 is the amino acid sequence of human FTO (gi|122937263).
SEQ ID NO: 2 is the amino acid sequence of chimpanzee FTO which shares 99% sequence identity with human FTO (gi|114662524).
SEQ ID NO: 3 is the amino acid sequence of macaque FTO which shares 93% sequence identity with human FTO (gi|109128525).
SEQ ID NO: 4 is the amino acid sequence of dog FTO which shares 91% sequence identity with human FTO (gi|73950384).
SEQ ID NO: 5 is the amino acid sequence of cow FTO which shares 88% sequence identity with human FTO (gi|119910109).
SEQ ID NO: 6 is the amino acid sequence of opossum FTO which shares 65% sequence identity with human FTO (gi|126296336).
SEQ ID NO: 7 is an amino acid sequence of mouse FTO which shares 87% sequence identity with human FTO (gi|18490097).
SEQ ID NO: 8 is an amino acid sequence of mouse FTO which shares 87% sequence identity with human FTO (gi|6753916).
SEQ ID NO: 9 is the amino acid sequence of rat FTO which shares 87% sequence identity with human FTO (gi|89337260).
SEQ ID NO: 10 is the amino acid sequence of fish FTO which shares 48% sequence identity with human FTO (gi|125821796).
SEQ ID NO: 11 is the amino acid sequence of frog FTO which shares 52% sequence identity with human FTO (gi|62859671).
SEQ ID NO: 12 is the amino acid sequence of human ABH3 (gi|21040275).

DETAILED DESCRIPTION OF THE INVENTION

The present inventors have purified recombinant FTO and identified FTO as a 2-oxoglutarate (2-OG) dependent oxygenase. Accordingly, the present invention provides a method for assaying FTO activity, the method comprising monitoring oxygenase activity of a FTO polypeptide. The present invention also provides the use of a FTO polypeptide in assay methods to identify modulators of FTO oxygenase activity and substrates that are oxidised by FTO.

The present inventors have found that FTO is homologous to the Fe(II) and 2-OG dependent oxygenases with particularly strong sequence similarity to the human DNA demethylase, ABH3, which has known activity as a demethylase on 1-methyladenine and 3-methylcytosine nucleic acid bases. The FTO polypeptide for use in the invention typically binds $Fe^{2+}$. Therefore, in one aspect of the invention, iron is used as a cofactor in the method for assaying FTO activity.

The FTO polypeptide for use in accordance with the invention typically has the ability to convert 2-OG and oxygen to succinate and carbon dioxide. Accordingly, in one aspect of the invention, the method for assaying FTO activity uses oxygen and/or 2-OG as co-substrates.

The FTO polypeptide may comprise the sequence shown in SEQ ID NO: 1, or an amino acid sequence having at least 40% sequence identity, for example at least 45% sequence identity, with SEQ ID NO: 1 in the double-stranded beta-helix (DSBH) domain or at least about 40%, for example at least about 50% or about 60% sequence identity with the amino acid sequence of SEQ ID NO: 1, over its entire length, typically greater than 70% or 80%, more typically greater than about 90% or 95%, such as about 99% sequence identity.

Sequence identity may be calculated using any suitable algorithm. For example, the UWGCG Package provides the BESTFIT program can be used to infer homology (for example used on its default settings) (Devereux et al. (1984) *Nucleic Acids Research* 12, p 387-395). The PILEUP and BLAST algorithms can be used to infer homology or line up sequences (typically on their default settings), for example as described in Latched (1993) J. Mol. Evol 36:290-300 or Latched et al. (1990) J. Mol. Biol. 215:403-10.

The FTO polypeptide may be a polypeptide encoded by any naturally occurring FTO gene. The naturally occurring FTO gene may comprise the sequence shown in SEQ ID NO: 1 or may be a variant of SEQ ID NO: 1. Such variants may include allelic variants and the deletion, modification or addition of single amino acids or groups of amino acids within the protein sequence, as long as the polypeptide retains 2-OG oxygenase activity. The polypeptide also preferably has a nuclear localisation signal, in particular where the activity of the polypeptide is monitored using a cell based assay. The nuclear localisation signal may be the FTO nuclear localisation signal sequence or a nuclear localisation signal sequence from another peptide.

The FTO polypeptide may be a homologue of FTO from a non-human species such as the chimpanzee (SEQ ID NO: 2), macaque (SEQ ID NO: 3), dog (SEQ ID NO: 4), cow (SEQ ID NO: 5), opossum (SEQ ID NO: 6), mouse (SEQ ID NO: 7 or 8), rat (SEQ ID NO: 9), fish (SEQ ID NO: 10), frog homologue (SEQ ID NO: 11) of FTO or a homologue from another organism, such green algae. The homologue of FTO may be a naturally occurring protein. The FTO polypeptide may have an amino acid sequence that does not occur in nature but which contains the deletion, modification or addition of single amino acids or groups of amino acids compared to a naturally occurring FTO sequence. For example, the FTO polypeptide may have at least about 40%, such as at least about 50%, 60%, 70%, 80%, 90%, 95% or 99% sequence identity with any one of SEQ ID NOs: 1 to 11.

Amino acid substitutions of any one of SEQ ID NOs: 1 to 11 may be made, for example from about 1, 2 or 3 to about 10, 20 or 30 substitutions. Conservative substitutions may be made, for example according to the following Table. Amino acids in the same block in the second column and preferably in the same line in the third column may be substituted for each other.

| | | |
|---|---|---|
| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

Variant polypeptides within the scope of the invention may be generated by any suitable method, for example by gene shuffling techniques.

The present invention also includes use of active portions, fragments, derivatives and functional mimetic of the polypeptides of the invention. An "active portion" of a polypeptide means a peptide which is less than said full-length polypeptide, but which retains 2-OG oxygenase activity. An active fragment of FTO may typically be identified by monitoring for 2-OG oxygenase activity as described in more detail below. Such an active fragment may be included as part of a fusion protein, e.g. including a binding portion for a different i.e. heterologous ligand.

The fragment may have at least about 50 amino acids or up to about 60, 70, 80, 100, 150, 200, 400 or 500 amino acids. In particular, but not exclusively, this aspect of the invention encompasses the situation when the protein is a fragment of the complete FTO protein sequence and may represent a catalytic region, capable of converting 2-OG to succinate and carbon dioxide. The catalytic cores of human, chimpanzee, macaque, dog, cow, opossum, mouse, rat, fish and frog FTOs are shown in SEQ ID NOs: 1 to 11. In one embodiment the fragment may comprise the catalytic core and the nucleotide-recognition lid that lies adjacent to the N-terminal end of the catalytic core.

The fragment may comprise any region from about amino acid 1 to about 505 of the amino acid sequence shown in SEQ ID NO: 1, such as from amino acid 2, 3, 4, 5 or 10 to amino acid 495, 500, 501, 502, 503 or 504. Useful fragments include N-terminal truncated fragments i.e., fragments comprising an N-terminal deletion, such as fragments comprising residues 30 to 505 or 60 to 505 of the amino acid sequence shown in SEQ ID NO: 1 and fragments comprising both N-terminal and C-terminal truncations, such as fragment comprising residues 30 to 33 or 60 to 330 of the amino acid sequence shown in SEQ ID NO: 1. Other suitable fragments may readily be identified, for example by comparing the FTO amino acid sequence to the amino acid sequence of one or more known 2-OG dependent oxygenase and identifying which regions are not homologous to regions having catalytic activity. The regions having catalytic activity are typically included in the active fragments. Such fragments can be used to construct chimeric molecules.

Fragments of any FTO polypeptide having at least about 60%, such as at least about 70%, 80%, 90%, 95%, 99% or 100% sequence identity to the amino acid sequence column in SEQ ID NO: 1 (for example, fragments of any naturally occurring or genetically engineered sequence discussed above including fragments of any one of SEQ ID NOs: 2 to 11) which fragments have oxygenase activity may also be used in an assay of the invention and are encompassed within the term "FTO polypeptide" used herein.

The FTO polypeptides may be synthetically prepared. The polypeptides may be chemically or biochemically modified, e.g. post-translationally modified. For example, they may be glycosylated or comprise modified amino acid residues. They may also be modified by the addition of histidine residues (typically six), or other sequence tags such as a maltose binding protein tag or intein tag, to assist their purification or by the addition of a nuclear localisation sequence to promote translocation to the nucleus or mitochondria, and or by post translational modification including hydroxylation or phosphorylation. Polypeptides of the invention may be GST or other suitable fusion polypeptides. The FTO polypeptide may also be modified by addition of fluorescent tags (such as green fluorescent protein) to enable visualization within cells or organelles or to aid purification of the protein or cells expressing FTO. Such modified polypeptides fall within the scope of the term "FTO polypeptide".

The polypeptides of the invention may be present in a partially purified or in a substantially isolated form. They may be mixed with carriers or diluents, which will not interfere with their intended use and still be regarded as substantially isolated. They may also be in a substantially purified form, in which case they will generally comprise at least about 90%, e.g. at least about 95%, 98% or 99%, of the proteins, polynucleotides, cells or dry mass of the preparation.

The polypeptides of the invention may be used in assays for 2-OG dependent oxygenase activity, for example to identify modulators, such as inhibitors or activators of hydroxylase activity. The inhibitors may be selective inhibitors or activators.

The FTO polypeptides may be used in assays for 2-OG oxygenase activity in the absence of a prime substrate (i.e, a non 2-OG substrate). The FTO polypeptides may also be used to determine oxygenase activity in the presence of one or more suitable substrates. In addition, the present invention provides methods for identifying substrates of FTO.

FTO used in a method of the invention may be recombinant FTO or naturally occurring FTO. Preferably, recombinant FTO is used especially where FTO is required for purposes requiring large (>1 mg) amounts of protein such as for biophysical assays or for high throughput analyses. Recombinant FTO may be produced using standard expression vectors that comprise nucleotide sequences encoding FTO. Such expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for protein expression. Other suitable vectors would be apparent to persons skilled in the art. By way of further example in this regard we refer to Sambrook et al. 1989.

Methods of the invention may utilise cells that have been modified to express a FTO polypeptide as defined herein. The FTO may also be present in a cell extract or in a partially or substantially purified form.

Methods for Obtaining Purified FTO

The present inventors have found that it is possible to express a recombinant FTO in soluble and active form using a modified expression and purification method. The inventors have also demonstrated that purified recombinant FTO is a 2-OG dependent oxygenase. Accordingly, the invention provides a method for obtaining purified FTO and a method for assaying oxygenase activity of purified FTO.

A purified FTO polypeptide may be obtained by introducing an expression vector comprising a polynucleotide encoding a FTO polypeptide into a host cell.

Expression vectors are routinely constructed in the art and may for example involve the use of plasmid DNA and appropriate initiators, promoters, enhancers and other elements, such as for example polyadenylation signals which may be necessary and which are positioned in the correct orientation in order to allow full protein expression. Suitable vectors would be very readily apparent to those of skill in the art. Promoter sequences may be inducible or constitutive promoters depending on the selected assay format. The promoter may be tissue specific. Thus the coding sequence in the vector is operably linked to such elements so that they provide for expression of the coding sequence (typically in a cell). The term "operably linked" refers to a juxtaposition wherein the components described are in a relationship permitting them to function in their intended manner.

The vector may be, for example, a plasmid, virus or baculovirus vector. The vector is typically adapted to be used in a bacterial cell, such as E. coli. The vector may have an origin of replication. The vector may comprise one or more selectable marker genes, for example an ampicillin resistance gene in the case of a bacterial plasmid or a resistance gene for a fungal vector. Vectors may be used to transfect or transform a host cell, for example, a bacterial host cell, fungal host cell, an insect host cell, a mammalian, e.g. human host cell or a baculovirus host cell. The bacterial host cell is preferably a strain of E. coli, for example BL21 (DE3).

A method of producing a purified FTO polypeptide is provided by the invention. The method typically comprises culturing host cells comprising an expression vector encoding a FTO polypeptide and isolating the FTO polypeptide from the cells. The host cells may typically be cultured, for example, at a temperature of from about 15° C. to about 37° C. The polypeptide may be isolated by lysing the cells and extracting the protein from the lysis buffer. The lysis buffer typically comprises from about 250 mM to about 700 mM salt, e.g. NaCl, such as from about 400 mM to about 600 mM, e.g. 500 mM. A method of producing a FTO polypeptide according to the invention may further comprise introducing a polynucleotide or vector according to the invention into the host cell. The FTO polypeptide is comprised in the soluble fraction obtained upon lysis of the cell culture. The polypeptide may be further purified from the soluble fraction, for example by affinity purification, such as via an affinity tag fused to the truncated 2-OG dependent oxygenase.

Methods for introducing polypeptides and vectors into host cells are well known in the art, and include electroporation and heat shock techniques without limitation. Expression of the truncated polypeptide may then be achieved by culturing the host cells at a suitable temperature. The cells expressing recombinant FTO are preferably kept at between about 15° C. and about 30° C., for example at about 20° C. or about 28° C. to induce expression of recombinant FTO. Where the host cells are bacteria, such as E. coli, the cells may be cultured in 2TY medium. IPTG may be added to the culture medium, either throughout the period of incubation (or growth period) or in the final stages of the incubation period.

The lysis buffer containing a high salt level is typically used to lyse the cells after centrifuging the cells to remove the cell culture medium. The buffer typically contains from about 250 mmol salt, e.g. NaCl, to about 700 mmol salt, for example from about 400 to about 600 mmol NaCl, such as about 500 mmol NaCl. The extraction buffer may comprise detergents, such as Triton X-100 and/or SDS (typically 1%), and/or lysozyme. Glycerol may be present in the lysis buffer, typically at a concentration of from about 5% to about 20%, such as about 10%. The lysis buffer typically has a pH greater than about 7.5, for example from about 7.6 to about 8.1, from about 7.8 to about 8.0, more preferably about 7.9. The lysis buffer may be suitable for sonication of the cells. Tris may also be present in the lysis buffer, for example at a concentration of from about 10 mmol to about 100 mmol, such as about 20 mmol.

After lysis, the cells may be centrifuged. After centrifugation, the supernatant represents the soluble fraction. The concentration of proteins present in the soluble fraction depends on the quantity of extraction buffer used. The FTO is present in the soluble fraction in an amount sufficient for it to be purified. This can be determined by SDS PAGE. If it is possible to detect the truncated enzyme by SDS PAGE, there is sufficient enzyme present for purification.

FTO polypeptides of the invention may be purified by standard techniques known in the art. For example, where the polypeptide comprises a His tag, it may be purified using a his-binding resin by following the manufacturer's instructions (e.g. Novagen) or by other means such as ion exchange chromatography. The purification procedure may comprise the following steps. The cells expressing a recombinant polypeptide of the invention may be pelleted and resuspended in a suitable buffer and then sonicated to break up the cells.

The cell debris is separated from the soluble material by centrifugation and the soluble fraction is loaded on a his-binding column. After washing the column with binding buffer and wash buffer, the bound protein is eluted from the column using elution buffer. The binding, wash and elution buffers each typically comprise 0.5M NaCl. It is not necessary to add additional salt. The eluted protein is then concentrated and incubated with thrombin (typically at a concentration of 1 Umg$^{-1}$ at 4° C. for 16 hours). The digested proteins are separated using a gel filtration column and the FTO eluted from the column is generally at least 90%, or at least 95% pure. The purified protein for use in the various assays described herein may be de-salted.

Assays

Our data show that FTO catalyses the conversion of 2-OG to succinate and carbon dioxide. This newly discovered activity of FTO means that, for the first time, assays for identifying inhibitors or stimulators/activators of FTO activity can be performed. Blocking or activating 2-OG oxygenase activity of FTO will result in weight modulation. Any suitable assay may be carried out to identify modulators of FTO oxygenase activity and in particular of 2-OG oxygenase activity. A number of different examples of suitable assays are described below. In one embodiment, the assays utilise a human FTO polypeptide as described herein. FTO polypeptides may be provided either in purified or unpurified form, for example as cellular extracts or by purification of the relevant polypeptides from such extracts. Alternatively, the relevant component can be expressed using recombinant expression techniques and purified for use in the assay. Alternatively, the components may be expressed recombinantly in a cell for use in cell-based assays.

Assay Methods

The FTO polypeptides may be used in an assay for oxygenase activity, such as 2-OG oxygenase activity. These polypeptides are also useful in assays for identifying an agent, which modulates, such as inhibits or activates, FTO oxygenase activity. The method comprises contacting a FTO polypeptide and a test substance, such as a potential inhibitor, in the presence of one or more co-substrate and optionally a prime substrate. The test substance and FTP polypeptide are typically contacted under conditions suitable for oxygenase activity. Suitable co-substrates include oxygen, for example, dioxygen, and 2-oxoacids such as 2-OG. Preferably, the co-substrate is 2-OG. In addition to oxygen or a 2-oxoacid, a reducing agent, such as ascorbate may also be used as a co-substrate. The components of the assay are contacted under conditions in which the enzyme acts on the co-substrate in the absence of the test substance and determining the extent of co-substrate modification. Alternatively, oxidation of the prime substrate may be monitored. Assays that detect binding to FTO in the absence of catalytic turnover may also be used. Such assays may employ techniques such as chromatography, NMR, MS or fluorescence spectroscopy. The co-substrate may be modified, e.g. 2-OG, or consumed, e.g. oxygen or ascorbate, by FTO. Demethylation activity may be monitored by measuring formaldehyde release Suitable methods for measuring formaldehyde release are known in the art. Such methods are, for example, described in Kleeberg and Klinger (1982) J. Pharmacol. Methods 8: 19-31, Trewick et al. (2002) Nature 419: 174-178 and Tsukada et al. (2006) Nature 439: 811-816. The assay may also be used to detect substances that increase the activity of the 2-OG dependent oxygenase by assaying for increases in activity. Suitable assays have been described in the art for other 2-OG dependent oxygenases.

Such assays of the present invention may be used to identify inhibitors of oxygenase activity and are thus preferably carried out under conditions under which FTO is active as an oxygenase including in the absence of the test substance. The FTO oxygenase activity in the presence of the test substance is compared to FTO oxygenase activity in the absence of the test substance to determine whether the test substance is an inhibitor of FTO oxygenase activity. In the alternative, the assays may be used to look for promoters of FTO oxygenase activity, for example, by looking for increased conversion of co-substrate and/or hydroxylation of substrates compared to assays carried out in the absence of a test substance. The assays may also be carried out under conditions in which oxygenase activity is reduced or absent, such as under hypoxic conditions, and the presence of or increased activity could be monitored under such conditions.

The assays of the invention may also be used to identify inhibitors or activators which are specific for FTO and which do not have activity or are less active with other 2-OG oxygenases, for example, such as the procollagen hydroxylases, human ABHs (AlkB homologues), methyl lysine demethylases, hypoxia inducible factor (HIF) asparaginyl or prolyl hydroxylases. Conversely, the assays of the invention may be used to identify inhibitors or activators specific for one or more 2-OG dependent oxygenase, for example, such as HIF asparaginyl or prolyl hydroxylases, which do not inhibit FTO.

The assays of the invention may also be used to identify inhibitors or activators which are specific for FTO activity at a particular substrate or residue within a substrate.

In medicinal applications, for example, it is often advantageous to modulate oxygenase activity of a single enzyme or group of enzymes. Assays of the invention may therefore be used to identify agents which selectively modulate activity of FTO relative to a second 2-OG dependent oxygenase, including but not limited to lysyl, prolyl, asparaginyl and arginyl demethylases, the HIF hydroxylases, including FIH, PHD1, PHD2 and PHD3, AlkB, ABH1, ABH2, ABH3, procollagen prolyl and lysyl hydroxylases, the phosphatidyl serine receptor (Jmjd6), Mina53 and 2-OG oxygenases that have been characterized as Jmj domain proteins according to the SMART database including, but not limited to lysyl demethylases.

Such selectivity screens may be used to identify selective inhibitors of FTO or selective inhibitors of other enzymes, i.e. inhibitors that are more potent inhibitors of FTO activity than of activity of the other enzyme or inhibitors that are less potent inhibitors of FTO activity than of activity of the other enzyme. Where the inhibitor is a selective inhibitor of FTO activity it may have no effect on the activity of the other enzyme or may exhibit only a low level of inhibition, such as less than about 50% inhibition on activity of the other enzyme. Where the inhibitor is a selective inhibitor of activity of the non-FTO enzyme it may have no effect on the activity of FTO or may exhibit only a low level of inhibition, such as less than about 50% inhibition of FTO activity.

The selectivity screens may be carried out with purified enzymes, partially purified enzymes (such as in crude cell lysates) or in cells.

The invention provides the use of selective inhibitors in the manufacture of a medicament for the treatment of a condition associated with altered, i.e. enhanced or reduced, 2-OG dependent oxygenase activity, such as FTO oxygenase activity.

It is also possible, using the method of the invention to identify selective inhibitors when the prime substrate of one or more of the enzymes being tested is unknown. In this embodiment, generally it will be one or more of the enzymes that it is wished not to inhibit that is an enzyme that has an unknown substrate. The effect of a test agent on activity of an oxygenase may be determined in the absence of a substrate by determining whether or not the test agent affects, for example inhibits or stimulates, the rate of turnover of 2-OG by the oxygenase.

The assays of the present invention may use a substrate that is hydroxylated or otherwise oxidised by FTO. In particular, such substrates may be used in assays to monitor for the activity of a modulator of FTO 2-OG oxygenase activity. The substrate may be a peptide or nucleic acid substrate. The nucleic acid substrate may be DNA or RNA. Oligonucleotide substrates may be used. The DNA is preferably nuclear DNA, but may be mitochondrial DNA. Preferably the nucleic acid substrate is methylated at one or more residues.

Any suitable substrate which is hydroxylated, or more generally oxidised, by FTO, with FTO typically having the amino acid sequence or a variant of SEQ ID NO: 1, may be used. Some substrates of 2-OG dependent oxygenases are well known in the art. The substrate may be a naturally occurring protein or a recombinant or synthetic protein or a nucleic acid. Fragments and variants of naturally occurring substrate proteins or nucleic acids which include the site of oxidisation by FTO may be used as substrates in the assay of the invention.

In an assay to identify a selective inhibitor of FTO, or another oxygenase, different substrates may be used for FTO and for the other oxygenase(s).

The methods of the invention may be used to detect novel substrates of FTO 2-OG dependent oxygenase activity. In such an assay a test substrate is used and the detection of hydroxylase activity indicates that hydroxylation of the test substrate has occurred and, accordingly, that the test substrate is a substrate of the FTO. Such assays may be carried out with isolated components, semi-purified extracts or in whole cells.

The test substrate may be a nucleic acid, nucleic acid derivative or analogue, such as a methylated nucleic acid, or may be a protein or peptide, such as a methylated protein or peptide. The methylated nucleic acid, protein or peptide may be associated with a gene, protein or peptide involved in weight modulation. For example, the nucleic acid may be a part of the gene or a mRNA transcribed from the gene or the peptide or protein may be encoded by the gene. Examples of genes and peptides involved with weight modulation include the agouti gene and agouti related peptide and the neuropeptide Y gene and neuropeptide Y related peptide gene and the following peptides and the genes encoding them: leptin, proopiomelanocortin, orexin, galanin, PYY, cholecystokinin, glucagon-related peptide-1 and insulin.

Inhibitors of FTO activity, including but not limited to 2-OG analogues such as N-oxoalylglycine and transition metals such as Zinc, magnesium, manganese, cobalt and nickel, may be used to enable identification of a FTO substrate by stabilising the interaction between FTO and the substrate and then identifying the substrate, or binding partner, bound to FTO. Standard methods may be used to identify the substrate, or binding partner. Examples of techniques that may be used techniques involving mass spectroscopy or antibodies or other standard reagents and methodologies used within the art of proteomics. Alternatively binding assays or cell-based assays may be used.

Methods for Monitoring Modulation

The precise format of any of the screening or assay methods of the present invention may be varied by those of skill in the art using routine skill and knowledge. The skilled person is well aware of the need to additionally employ appropriate controlled experiments. The assays of the present invention may involve monitoring for hydroxylation of a suitable substrate, monitoring for the utilisation of substrates and co-substrates, monitoring for the production of the expected products between the enzyme and its substrate. Assay methods of the present invention may also involve screening for the direct interaction between components in the system. Alternatively, assays may be carried out which monitor for downstream effects mediated by the substrate, such as substrate mediated transcription using suitable reporter constructs or by monitoring for the upregulation of genes or alterations in the expression patterns of genes known to be regulated directly or indirectly by the substrate.

Various methods for determining oxygenase activity either directly or indirectly are known in the art. Any suitable method may be used for determining 2-OG dependent oxygenase activity of FTO such as by substrate or co-substrate utilisation, product appearance such as peptide/nucleic acid hydroxylation/demethylation or down-stream effects mediated by hydroxylated/demethylated or non-hydroxylated products.

The substrate, enzyme and potential inhibitor compound may be incubated together under conditions which, in the absence of inhibitor provide for hydroxylation/demethylation of the substrate, and the effect of the inhibitor may be determined by determining hydroxylation/demethylation of the substrate. This may be accomplished by any suitable means. Small polypeptide or polynucleotide substrates may be recovered and subjected to physical analysis, such as mass spectrometry, radiography or chromatography, or to functional analysis. Such methods are known as such in the art and may be practiced using routine skill and knowledge. For example, the LC-MS assay described in the Examples may be used. Determination may be quantitative or qualitative. In both cases, but particularly in the latter, qualitative determination may be carried out in comparison to a suitable control, e.g. a substrate incubated without the potential inhibitor.

In alternative embodiments, reporter constructs may be provided in which promoters mediated by a substrate are provided operably linked to a reporter gene. Any suitable reporter gene could be used, such as for example enzymes which may then be used in colorometric, fluorometric, fluorescence resonance or spectrometric assays.

In the assay methods described herein, typically the FTO and the substrate are contacted in the presence of a co-substrate, such as oxygen and/or a 2-oxoacid, such as 2-OG and/or dioxygen. Hydroxylase/demethylase activity may be determined by determining turnover of one or more of the co-substrates, such as oxygen, 2-OG and/or ascorbate. This may be achieved by determining the presence and/or amount of reaction products, such as hydroxylated substrate or succinic acid. The amount of product may be determined relative to the amount of substrate. For example, in such embodiments the substrate may be a polypeptide and, for example, the product measured may be hydroxylated/demethylated polypeptide or nucleic acid. For example, the extent of hydroxylation/demethylation may be determined by measuring the amount of hydroxylated/demethylated polypeptide/nucleic acid, succinate, carbon dioxide, or formaldehyde generated in the reaction, or by measuring the depletion of 2-OG or dioxygen. Methods for monitoring each of these are known in the scientific literature, for example in Myllyharju et al. (1991) EMBO J. 16(6): 1173-1180 or as in Cunliffe et al. (1986) Biochem. J. 240: 617-619.

Unused 2-OG may be derivatised by chemical reagents, exemplified by but not limited to hydrazine derivatives and ortho-phenylene diamine derivatives, to give indicative chromophores or fluorophores that can be quantified and used to indicate the extent of hydroxylation of the test polypeptide. Dissolved oxygen electrodes, exemplified by but not limited to a "Clarke-type" electrode or an electrode that uses fluorescence quenching, may be used to follow the consumption of oxygen in an assay mixture, which can then be used to indicate the extent of hydroxylation of the test polypeptide in an analogous manner to the above.

The fluorescent product of the reaction of ortho-phenylenediamine (OPD) with the α-ketoacid motif of 2-OG is 3-(2-Carboxyethyl)-2(1H)-quinoxalinone. This fluorescent product can be readily detected by standard equipment such as that manufactured by for example Molecular Devices, Tecan, BMG Labtechnologies, Jasco and Perkin Elmer and there is extensive precedent demonstrating that the production of fluorescent products can be used in high-throughput screens.

The fluorescent product is generally detected with the excitation filter set as from about 300 nm to about 400 nm, preferably from about 335 to about 345 nm, most preferably at about 340 nm. The emission filter is generally at from about 400 to about 450 nm, preferably from about 415 to about 425 nm, most preferably at about 420 nm.

This assay procedure lends itself to high-throughput formats, such as multi-well plate formats e.g. 96-, 384-, or 1536-well plate formats.

Further, the nature of the fluorescent product can be tuned by modifying the nature of the derivatisation reagent used. For example, the sensitivity of the method may be increased by using either 1,2-dimethoxy-4,5-diaminobenzene, or 1,2-methylenedioxy-4,5-diaminobenzene.

The precise format of any of the screening or assay methods of the present invention may be varied by those of skill in the art using routine skill and knowledge. The skilled person is well aware of the need to additionally employ appropriate control experiments. Activity is measured by derivatisation of 2-OG with OPD or other aromatic diamines, such as 1,2-dimethoxy-4,5-diaminobenzene or 1,2-methylenedioxy-4,5-diaminobenzene, such that the derivative gives improved sensitivity compared to use of OPD (Willing et al. Journal of Chromatography B (2003) 383-392, Nakamura et al. Chem. Pharm Bull. (1987) 687-692).

The assay is carried out under conditions suitable for hydroxylation/oxidation of the substrate by the oxidase. Accordingly, 2-OG is present in the assay. The assay mixture may also contain iron, preferably ferrous iron.

Other components may be added to the assay mixtures. For example, a reducing agent such as ascorbate, a thiol such as dithiothrietol (DDT), β-mercaptoethanol, N-acetylcysteine or phenol may be added to the assay to help maintain enzyme structure and/or catalase may be added to destroy any $H_2O_2$ that might be produced. However, the assay will work in the absence of a reducing agent or catalase.

Assays are typically carried out at a temperature of from about 25° C. to about 40° C., for example at a temperature of from about 30° C. to about 39° C., or from about 35° C. to about 38° C. or about 37° C. The pH of the assay mixture is typically between about pH 7 to about pH 9, for example from about pH 7.5 to about pH 8. Suitable buffers, such as Tris or HEPES, may be used to maintain the pH of the assay mixture.

Typically, assays are carried out under normoxic conditions. The assay may also be carried out under conditions in which hydroxylation or oxidation is reduced or absent, such as under hypoxic conditions, in order to detect modulation of oxygenase activity by an agent which enhances hydroxylation/oxidation.

Alternatively, the end-point determination may be based on conversion of the substrate or substrate fragments (including synthetic and recombinant peptides or nucleic acids) derived from the polypeptide or nucleic acid substrate into detectable products. Substrates may be modified to facilitate the assays so that they can be rapidly carried out and may be suitable for high throughput screening.

For example, reverse phase HPLC (C-4 octadecylsilane column), as exemplified herein, may be used to separate starting synthetic peptide substrates from the products. Modifications of this assay or alternative assays for oxygenase activity may employ, for example, mass spectrometric, spectroscopic, and/or fluorescence techniques as are well known in the art (Masimirembwa C. et al. Combinatorial Chemistry & High Throughput Screening (2001) 4 (3) 245-263, Owicki J. (2000) J. Biomol. Screen. 5 (5) 297-305, Gershkovich A et al. (1996) J. Biochem. & Biophys. Meths. 33 (3) 135-162, Kraaft G. et al. (1994) Meths. Enzymol. 241 70-86). Fluorescent techniques may employ versions of the substrate to modified in such as way as to carry out or optimise spectroscopic or fluorescence assays.

Binding of a molecule which discriminates between the hydroxylated and non-hydroxylated or demethylated form of a polypeptide or other substrate may be assessed using any technique available to those skilled in the art, which may involve determination of the presence of a suitable label.

Assay methods of the present invention may also take the form of an in vivo assay or an assay carried out on ex vivo cells from an animal, such as a mammal (including human) or an insect. The assay may be performed in a cell line such as a yeast or bacterial strain or an insect or mammalian cell line in which the relevant polypeptides or peptides are expressed from one or more vectors introduced into the cell. Alternatively, the assay may be carried out on a mammalian cell that expresses endogenous FTO or in which FTO is over-expressed.

The FTO polypeptide used in a cell-based assay of the invention preferably comprises a nuclear localisation signal.

Test Compounds

Agents, which may be screened using the assay methods described herein, may be natural or synthetic chemical compounds used in drug screening programmes. Extracts of plants, microbes or other organisms, which contain several, characterised or uncharacterised components may also be used.

Combinatorial library technology (including solid phase synthesis and parallel synthesis methodologies) can provide an efficient way of testing a potentially vast number of different substances for ability to modulate an interaction. Such libraries and their use are known in the art, for all manner of natural products, small molecules and peptides, among others. The use of peptide libraries may be preferred in certain circumstances. Various commercial libraries of compounds are also available. There are computational methods for screening these libraries (processes sometimes referred to as virtual screening) that can identify lead structures for inhibition.

Potential inhibitor compounds (i.e. antagonists) may be polypeptides, small molecules such as molecules from commercially available libraries, including combinatorial libraries, or the like. Small molecule compounds, which may be used, include 2-OG analogues, or substrate analogues, which inhibit the action of the enzyme. Small molecule compounds, and other types of compound, that may be used include all known 2-OG oxygenase inhibitors such as those already known to inhibit HIF hydroxylases (see for example WO02/074981 and WO03/080566) and procollagen prolyl hydroxylases.

Potential promoting agents may be screened from a wide variety of sources, particularly from libraries of small compounds, which are commercially available. Oxygen-containing compounds may be included in candidate compounds to be screened, for example 2-OG analogues. Any agents currently used for treating obesity (Cooke and Bloom, Nature Reviews Drug Discovery 2006) and type 2 diabetes may affect the activity of FTO and may be used as candidate agents.

Since naturally occurring compounds, including TCA cycle intermediates such as fumarate, are known inhibitors of 2-OG oxygenases they may inhibit FTO, possibly in a manner that is of physiological relevance, including in some cancers where fumarate is known to be upregulated as a consequence of the Warburg effect.

A test compound which increases, potentiates, stimulates, disrupts, reduces, interferes with or wholly or partially abolishes hydroxylation/oxidation of the substrate and which may thereby modulate activity, may be identified and/or obtained using the assay methods described herein.

Agents which increase or potentiate hydroxylation/oxidation (i.e. agonists), for example prolyl or asparaginyl hydroxylation, may be identified and/or obtained under conditions which, in the absence of a positively-testing agent, limit or prevent hydroxylation/oxidation. Such agents may be used to potentiate, increase, enhance or stimulate the oxygenase activity of FTO.

In various aspects, the present invention provides an agent or compound identified by a screening method of the invention to be a modulator of FTO oxygenase activity e.g. a substance which inhibits or reduces, increases or potentiates the activity of FTO.

The test agent may compete with 2-OG or a FTO substrate at the FTO active site and/or binds to the metal at the FTO active site. The test agent may comprise a metal ion such as, but not limited to, manganese, cobalt, zinc or nickel ions. Alternatively, the mode of inhibition may be via an allosteric interaction.

The test agent may be a reducing agent. Reducing agents typically act as activators of 2-OG oxygenase activity, typically in vitro. An activator of oxygenase activity may be any species that increases oxygenase activity of a FTO polypeptide either in vitro or in vivo. Reducing agents that may be used include ascorbate and analogues of ascorbate and reducing agents of the thiol chemical families, such as dithiothreitol or phosphine (e.g. triscarboxyethylphosphine).

Following identification of a modulator, the substance may be purified and/or investigated further (e.g. modified) and/or manufactured. A modulator may be used to obtain peptidyl or non-peptidyl mimetics, e.g. by methods well known to those skilled in the art and discussed herein. A modulator may be modified, for example to increase selectivity, as described herein. It may be used in a therapeutic context as discussed below.

For therapeutic treatment, the modulator may be used alone or in combination with any other therapeutically active substance or treatment.

The compounds which are acids can be present in the form of salts, such as sodium salts. The compounds may also be present in the form of derivatives such as the dimethyl ester, diethyl ester, monoethyl ester or di- or mono-amide. In certain instances these derivatives may be preferred, for example when inhibition of the enzyme within a cell of an organism is required.

Compounds which modulate 2-OG oxygenases may be useful as agents of the invention, for example, in the treatment of weight disorders as described herein, or may be used as test substances in an assay of the invention. The test compound may be known to act as an inhibitor of a 2-OG oxygenase other than FTO. For example, the test agent may be an inhibitor of procollagen prolyl hydroxylase, hypoxia inducible factor, prolyl and asparaginyl hydroxylases, collagen prolyl hydroxylase, gibberellin C-20 oxidase, a nucleic acid demethylase such as AlkB or a human AlkB homologue, a protein demethylase, such as a tri-, di-, mono-methyl lysine or arginine residue demethylase, another human or animal 2OG oxygenase involved in metabolism or regulation, or a plant 2-OG hydroxylase. Many inhibitors of 2-OG oxygenases are known in particular for human prolyl hydroxylases. N-oxaloglycine and its derivatives are suitable examples. Glycine or alanine derivatives and 2-oxoacid analogues may also be used.

Compounds which modulate 2-OG oxygenases, and families of such compounds, are known in the art, for example in Aoyagi et al. (2002) Hepatology Research 23 (1): 1-6, Aoyagi et al. (2003) Free Radical Biology and Medicine 35:410 Suppl. 1, Philipp et al. (2002) Circulation 106 (19): 1344 Suppl. S, Ivan et al. (2002) PNAS USA 99 (21): 13459-13464, Nwogu et al. (2001) Circulation 104 (18): 2216-2221, Myllyharju and Kivirikko (2001) Ann Med 33 (1): 7-21, Ohta et al. (1984) Chemical and Pharm Bulletin 32 (11): 4350-4359, Franklin et al. (2001) Biochem J. 353: 333-338, Franklin (1997) Int J. Biochem Cell Biol 29 (1): 79-89, Dowell et al. (1993) Eur J Med Chem 28 (6): 513-516, Baader et al. (1994) Biochem J. 300: 525-530, Baader et al. (1994) Eur J Clin Chem and Clin Biol 32 (7): 515-520, Bickel et al. (1998) Hepatology 28 (2): 404-411, Bickel et al. (1991) J. Hepatology 13: S26-S34 Suppl. 3, U.S. Pat. No. 6,200,974, U.S. Pat. No. 5,916,898, US Patent Applications 2003-0176317, 2003-0153503 and 2004-0053977, WO 02/074981, WO 03/080566, WO 04/035812, Cunliffe et al. (1992) J. Med. Chem. 35:2652-2658, Higashide et al. (1995) J. Antibiotics 38:285-295, Cunliffe et al. (1986) Biochem. J. 239(2):311-315, Franklin et al. (1989) Biochem. J. 261(1):127-130, Friedman et al. (2000) PNAS USA 97(9):4736-4741, Wu et al. (1999) J. Am. Chem. Soc. 121(3): 587-588, DE-A-3818850, Wang et al. (2001) Biochemistry US:15676-15683 and Lerner et al. (2001) Angew Chem. Int. Edit. 40:4040-4041.

Suitable test compounds are disclosed in WO03/080566 and WO02/074981. Other suitable compounds include inhibitors of Fibrogen HIF hydroxylase. Fibrogen HIF hydroxylase inhibitors are disclosed in United States Patent Application Publication Nos: 20070042937, 20060276477, 20060270699, 20060258702, 20060258660, 20060251638, 20060183695, 20060178317 and 20060178316.

Other suitable test compounds include compounds of formula (I):

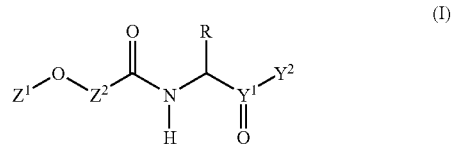

wherein
  $Y^2$ is selected from —OR' and —NR'R" wherein R' is hydrogen, or unsubstituted $C_{1-4}$ alkyl and R" is hydrogen, hydroxy or unsubstituted $C_{1-4}$ alkyl;
  $Y^1$ is selected from —C—, —S— and —S(O)—;
  $Z^2$ is selected from —C(O)— and —NR"— wherein R" is selected from hydrogen, hydroxy or unsubstituted $C_{1-4}$ alkyl;
  $Z^1$ is selected from hydrogen and unsubstituted $C_{1-4}$ alkyl; and
  R is a side chain of a naturally occurring amino acid.

Preferably $Y^1$ is —C— and $Y^2$ is —OH or —NH$_2$. Most preferably $Y^1$ is —C— and $Y^2$ is —OH.

Preferably $Z^2$ is —C(O)— or —NR"— wherein R" is hydrogen, methyl or ethyl. More preferably $Z^2$ is —C(O)— or —NH—. Preferably $Z^1$ is hydrogen, methyl or ethyl, more preferably hydrogen. Most preferably $Z^2$ is —C(O)— and $Z^1$ is hydrogen, methyl or ethyl.

Preferably R is a side chain of alanine, valine, leucine or phenylalanine. Preferably R is a side chain of valine, leucine or phenylalanine. More preferably R is a side chain of phenylalanine, i.e. —CH$_2$Ph.

L-stereoisomers or D-stereoisomers of these compounds may be used.

An exemplary synthetic scheme used to obtain test compounds of formula (I) is shown below in Scheme 1. Here an amino acid is reacted with an oxalyl chloride in order to produce a compound of formula (I). In this scheme the amino acid used is phenylalanine, although it will be apparent that the same general reaction will occur with other amino acids. The first reaction yields a protected compound of the invention (the dimethyl ester form). The diacid form is easily generated through reaction with aqueous sodium hydroxide.

Scheme 1:

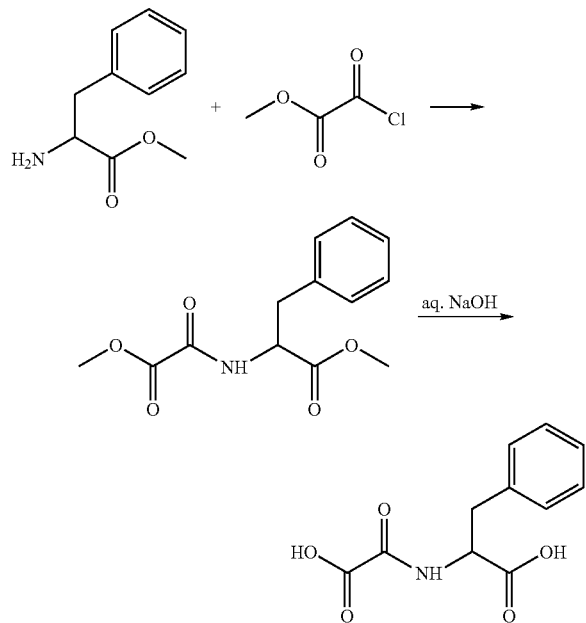

Compounds in which X is —O— or —S— or Z is other than —CO—CO—OH may by synthesised as described in Mole et al. (2003) Bioorg. Med. Chem. Lett. 13, 2677-2680 and Cunliffe et al. J. Med. Chem. (1992) 35 2652-2658.

Krebs cycle intermediates such as succinate and fumarate act as inhibitors of FTO demethylase activity. Therefore analogues of succinate and fumarate may be used to inhibit FTO activity.

Therapeutic Applications

A compound, substance or agent which is found to have the ability to affect the oxygenase activity of FTO has therapeutic and other potential in a number of contexts, as discussed. In particular modulators of FTO activity may be used in the treatment or prevention of diseases associated with weight gain or weight loss. The modulators may prevent or reverse weight gain in overweight patients. The modulators may prevent weight loss or promote weight gain in underweight patients. The modulators may also be administered to individuals having a weight within the normal healthy range (typically a body mass index of about 19 to about 25) in order to prevent weight gain, for example, where those individuals have an allelic variant of the FTO gene, which allelic variant is associated with obesity. In this embodiment, the modulators are used to prevent weight gain and associated diseases or disorders.

Diseases and disorders associated with weight gain that may be treated or prevented by administering a modulator of FTO activity include obesity (a body mass index over 30), cancer (in particular colon cancer, prostate cancer, cancer of the rectum, breast cancer and endometrial cancer), cardiovascular disease (including heart attack and congestive heart failure), hypertension, high cholesterol levels, insulin resistance, type II diabetes, gallstones, sleep apnea, osteoarthritis, gout, dyslipidemia, Pickwickian syndrome and infertility Disorders associated with weight loss that may be treated or prevented by administering a modulator of FTO activity include anorexia nervosa, bullemia, undernutrition, osteoporosis, infertility, impaired immunocompetence, AIDS or weight loss in patients on anti-cancer medication.

Modulators of FTO activity may also be used in the treatment or prevention of cancer. This is because of the ability of FTO to repair DNA.

For therapeutic treatment, an FTO modulator may be used in combination with any other active substance, e.g. for treatment in weight control, diabetes, and cardiovascular disease.

An agent identified using one or more primary screens (e.g. in a cell-free system) as having ability to modulate oxygenase activity may be assessed further using one or more secondary screens.

Generally, an agent, compound or substance which is a modulator according to the present invention is provided in an isolated and/or purified form, i.e. substantially pure. This may include being in a composition where it represents at least about 90% active ingredient, more preferably at least about 95%, more preferably at least about 98%. Any such composition may, however, include inert carrier materials or other pharmaceutically and physiologically acceptable excipients, such as those required for correct delivery, release and/or stabilisation of the active agent. As noted below, a composition according to the present invention may include in addition to a modulator compound as disclosed, one or more other molecules of therapeutic use, such as treatment in weight control, diabetes, and cardiovascular disease.

Products Obtained by Assays of the Invention

The invention further provides compounds obtained by assay methods of the present invention, and compositions comprising said compounds, such as pharmaceutical compositions wherein the compound is in a mixture with a pharmaceutically acceptable carrier or diluent. Examples of suitable carriers or diluents are given in, for example, "Harrison's Principles of Internal Medicine". The carrier may be liquid, e.g. saline, ethanol, glycerol and mixtures thereof, or solid, e.g. in the form of a tablet, or in a semi-solid form such as a gel formulated as a depot formulation or in a transdermally administrable vehicle, such as a transdermal patch.

The invention further provides a method of treatment which includes administering to a patient an agent which interferes with FTO oxygenase activity. Such agents may include inhibitors or activators of FTO oxygenase activity.

The therapeutic/prophylactic purpose may be related to the treatment of a condition associated with reduced or suboptimal or increased FTO levels or activity, or conditions in which have normal FTO levels, but where a modulation in activity such as an increase or decrease in FTO oxygenase activity is desirable. For example, FTO activity may be modulated in the treatment of disorders associated with undesirable weight loss or gain.

A therapeutically effective amount of an agent is typically administered to a subject in need thereof. A therapeutically effective amount is an amount which ameliorates the symptoms of the condition or lessens the suffering caused to the subject by the condition. A therapeutically effective amount for treating or preventing weight gain or a disorder associated with weight gain, such as obesity, is typically an amount that reduces weight gain, for example, an amount that maintains the weight of the patient or induces weight loss. Alternatively, a therapeutically effective amount may be an amount that induces weight loss. A therapeutically effective amount for treating or preventing weight loss or a disorder associated with weight loss, such as anorexia, is typically an amount that reduces weight loss, for example, an amount that maintains the weight of the patent or alternatively induces weight gain.

Pharmaceutical Compositions

In various further aspects, the present invention thus provides a pharmaceutical composition, medicament, drug or other composition for such a purpose, the composition comprising one or more agents, compounds or substances as described herein, including inhibitors or activators of 2-OG dependent oxygenase activity, the use of such a composition in a method of medical treatment, a method comprising administration of such a composition to a patient, e.g. for treatment (which may include preventative treatment) of a medical condition as described above, use of such an agent compound or substance in the manufacture of a composition, medicament or drug for administration for any such purpose, e.g. for treatment of a condition as described herein, and a method of making a pharmaceutical composition comprising admixing such an agent, compound or substance with a pharmaceutically acceptable excipient, vehicle or carrier, and optionally other ingredients.

In one embodiment the method for providing a pharmaceutical composition may typically comprise:
(a) identifying an agent by an assay method of the invention; and
(b) formulating the agent thus identified with a pharmaceutically acceptable excipient.

The pharmaceutical compositions of the invention may comprise an agent, polypeptide, polynucleotide, vector or antibody according to the invention and a pharmaceutically acceptable excipient.

Whatever the agent used in a method of medical treatment of the present invention, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors.

An agent or composition may be administered alone or in combination with other treatments, either simultaneously or sequentially dependent upon the condition to be treated, e.g. as described above.

Pharmaceutical compositions according to the present invention, and for use in accordance with the present invention, may include, in addition to active ingredient, a pharmaceutically acceptable excipient, carrier, buffer, stabiliser or other materials well known to those skilled in the art. In particular they may include a pharmaceutically acceptable excipient. Such materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Liposomes, particularly cationic liposomes, may be used in carrier formulations. Examples of techniques and protocols mentioned above can be found in Remington's Pharmaceutical Sciences, 16th edition, Osol, A. (ed), 1980.

The substance or composition may be administered in a localised manner to a particular site or may be delivered in a manner in which it targets particular cells or tissues, for example using intra-arterial stent based delivery.

Targeting therapies may be used to deliver the active substance more specifically to certain types of cell, by the use of targeting systems such as antibody or cell specific ligands. Targeting may be desirable for a variety of reasons, for example if the agent is unacceptably toxic, or if it would otherwise require too high a dosage, or if it would not otherwise be able to enter the target cells.

In a further embodiment the invention provides for the use of an agent of the invention in the manufacture of a medicament for the treatment of a condition associated with increased or decreased FTO oxygenase levels or activity. The condition may, for example include diseases associated with weight loss or gain.

All the documents cited herein are incorporated herein by reference.

The following Examples illustrate the invention.

EXAMPLES

Example 1

Selection of FTO for Analysis as a 2-OG Oxygenase

A sequence alignment of Fatso with ABH3 was created using a combination of secondary structure prediction (JPRED) and sequence conservation in order to build a homology model of FTO based on the reported ABH3 crystal structure (Sundheim et al. (2006) EMBO J. 25(14) 3389-3397) with MODELLER8V2. The model of FTO was then superimposed with ABH3 and the AlkB DNA demethylase from *E. coli* (Yu et al. (2006) Nature, 439, 879-884) for comparison. The sequence alignments, secondary structure predictions and structural model clearly show strong similarities among these three proteins. The DSBH scaffold is clearly present in FTO and the individual active site Fe(II) and 2OG binding residues are strictly conserved (e.g. His231 FTO, His191 ABH3, His131 AlkB; Asp233 FTO, Asp193 ABH3, Asp133 AlkB; His307 FTO, His257 ABH3, His187 AlkB; Arg316 FTO, Arg269 ABH3, Arg204 AlkB). In addition, residues involved the catalytic mechanism (i.e. Arg322 FTO, Arg275 ABH3 and Arg210 AlkB; Leu213 FTO and the hydroxylated Leu177 ABH3) and aromatic residues predicted to be involved in DNA base recognition (Tyr108 FTO and Tyr143 ABH3) are present.

The FTO sequence was thus detected as a homologue of AlkB homologues (ABHs) and other known 2-oxoglutarate dependent oxygenases, some of which catalyse demethylation of methylated nucleic acid sequences, and found to contain a double-stranded beta-helix (DSBH) motif and at least one C-terminal helical domain.

The DSBH motif is characteristic of 2-OG dependent oxygenases but many proteins that are not 2-OG dependent oxygenases also contain the DSBH motif. Such proteins include, but are not limited to, the JmjC family, some but not all of which are 2-OG dependent oxygenases (Clissold & Ponting (2001) Trends Biochem. Sci. 26: 7-9). The DSBH motif is also characteristic of the functionally diverse cupin superfamily (Dunwell et al. (2004) Phytochemistry 65: 7-17). The human protein pirin (Pang et al. (2004) J. Biol. Chem. 279: 1491-1498) also contains the DSBH motif, but is not a 2-OG dependent oxygenase. One 2-OG dependent oxygenase that contains the DSBH motif is FIH. Allelic variants of FTO have previously been correlated with weight gain, but FTO has not previously been identified as a 2-OG dependent oxygenase, nor as containing a DSBH structural motif.

The C-terminal helical domain of FTO is not known to be associated with 2OG oxygenases.

The sequence analyses also demonstrated that FTO exhibits the conserved 2-His-1-carboxylate facial triad used to bind Fe(II) and the basic residue (here Arginine) characteristics of the 2-OG iron-dependent oxygenases, as well as other features that place it within the sub-family of 2-OG oxygenases typified by AlkB.

Example 2

Cloning of FTO

The cDNA sequence encoding full-length mouse fto was amplified from Image clone IMGCLO4237261 using commercially synthesized oligonucleotide primers (Sigma-Genosys) mfto 1f (sequence: 5'-GCTAGCAT-GAAGCGCGTCCAGACC-3') SEQ ID NO: 14 and mfto1r (sequence: 5'-GAATTCCTAGGATCTTGCTTCCAGCAG-3') SEQ ID NO: 15 with restriction site overhangs in the following PCR reaction:

Conditions:

| | |
|---|---|
| Template DNA | 150 ng |
| mfto1f (10 µM) | 1 µl |
| mfto1r (10 µM) | 1 µl |
| MgCl$_2$ (50 mM) | 1 µl |
| dNTP's (10 mM each) | 1 µl (New England Biolabs) |
| 10x Polymerase buffer | 5 µl |
| PfuTurbo DNA polymerase | 1 µl (Polymerase buffer from Stratagene) |
| H$_2$O | added to a total volume of 50 µl |

Thermocycler Setup:

| | | |
|---|---|---|
| 95° C. | 2 min | |
| 95° C. | 1 min | |
| 50° C. | 1 min | } 25 cycles |
| 72° C. | 2.5 min | |
| 72° C. | 10 min | |

The completed PCR reaction was cleaned with a QIAquick PCR purification kit (QIAGEN) and a sample run on a 1% agarose gel with TAE buffer. The PCR product was digested with NheI and EcoRI (both New England Biolabs) at 37° C. in an overnight reaction:

| | |
|---|---|
| DNA | 1 µl |
| NheI (10000 units/ml) | 2 µl |
| EcoRI (20000 units/ml) | 2 µl |
| 10x EcoRI buffer | 5 µl |
| 100x BSA | 0.5 µl |
| H$_2$O | added to a total volume of 50 µl |

The reaction mixture was then run on a 1% agarose gel in TAE buffer, the band corresponding to the digested PCR product was excised and DNA extracted from the gel with a QIAquick gel extraction kit (QIAGEN).

The extracted DNA was ligated into similarly restricted and purified pET-28a vector (Novagen) using T4 DNA ligase (New England Biolabs) on ice over night:

| | |
|---|---|
| Vector | 50 ng |
| PCR product | 42 ng |
| 10xT4 buffer | 2 µl |
| T4 DNA ligase (400000 units/ml) | 0.5 µl |
| H$_2$O | added to a total volume of 20 µl |

4 µl of this reaction mixture was transformed into 50 µl *E. coli* XL10 Gold® cells (Stratagene) according to the manufacturer's instructions. Cells were grown on an LB plate containing 25 µg/ml Kanamycin at 37° C. overnight.

On the following day, 8 colonies were picked off the plate, resuspended in 5 ml 2YT medium containing 25 µg/ml Kanamycin each and incubated in an environmental shaker at 37° C. overnight.

Plasmids were isolated from these liquid cultures on the following day using a QIAprep Spin Miniprep kit (QIAGEN) and samples subjected to a control restriction digest with EcoRI and NheI at 37° C. for 3 hours:

| | |
|---|---|
| Miniprep DNA | 3 µl |
| NheI (10000 units/ml) | 1 µl |
| EcoRI (20000 units/ml) | 1 µl |
| 10x EcoRI buffer | 2 µl |
| 100x BSA | 0.2 µl |
| H$_2$O | added to a total volume of 20 µl |

Samples were analysed by 1% agarose gel and found to contain the mfto insert. One sample was submitted for external sequencing (Geneservice) and shown to contain the desired insert. This plasmid is referred to as mfto-pET-28a.

Example 3

Expression and Purification of FTO

Mfto-pET-28a was transformed into *E. coli* BL21-Gold (DE3) (Stratagene) according to the manufacturer's instructions and grown on an LB plate containing Kanamycin as above. Expression trials showed moderate soluble expression at 37° C., 28° C. and 21° C. and decreasing amounts of insoluble material with decreasing temperature.

For expression, a single colony was picked from the transformation plate, resuspended in 100 ml 2YT+Kanamycin medium and grown in an environmental shaker at 37° C. overnight. On the next day, 12 times 600 ml 2YT+Kanamycin were inoculated with 6 ml of the overnight culture each and grown in an environmental shaker at 37° C. until the cultures had reached $OD_{600}$ 1.0. At this stage, the cultures were shifted to 21° C. for an hour, after which IPTG was added to each to a final concentration of 0.25 mM. Incubation was continued at 21° C. for 9 hours, after which cells were collected (60 g total) by centrifugation and stored at −80° C.

The cell pellet was resuspended in 5 ml 10 mM HEPES pH 7.5, 0.5 M NaCl, 10 mM imidazole, 1 mM $MgCl_2$ containing a spatula tip of DNAseI per gram of cells. 30 mg Phenylmethylsulfonylfluoride (PMSF, protease inhibitor) was added and the cells lysed by sonication on ice. After centrifugation to remove debris (Beckman Avanti™ J-25 centrifuge, JA25.50 rotor, 22000 rpm, 20 minutes, 4° C.), supernatants were decanted, filtered through a 0.45 μm Omnipore filter (Millipore) and loaded onto a 10 ml His-Bind® column (Novagen) at a flow rate of 0.5 ml/min. The column was washed with 250 ml 10 mM HEPES pH 7.5, 0.5 M NaCl, 40 mM imidazole at 2 ml/min, followed by 100 ml 25 mM HEPES pH 7.5, 0.5 M NaCl, 40 mM imidazole, 5 mM ATP dipotassium salt at 2.5 ml/min: this step should remove E. coli chaperones binding to the peptide linker between His tag and Fto protein. After another wash of 100 ml of the initial washing buffer, bound protein was eluted with an isocratic elution using 35 ml 10 mM HEPES pH 7.5, 0.5 M NaCl, 500 mM imidazole at 2.5 ml/min.

Fractions containing FTO (>90% pure by SDS_PAGE analysis) were concentrated to a final volume of 3 ml using an Amicon-15 5000 Molecular-weight-cut-off ultrafiltration device and loaded onto a 300 ml Superdex S200 gel filtration column equilibrated in 10 mM HEPES pH 7.5, 0.05 M NaCl, 1 mM DTT. The gel filtration step was run at 3 ml/min with 10 ml fractions being collected starting at an elution volume of 70 ml.

Example 4

2-oxoglutarate Decarboxylation Assays with Purified FTO

FTO was tested for enzymatic activity using a 2-OG turnover assay (Kivirikko and Myllylä (1982) Methods in Enzymology 82: 4412-4421). FTO was incubated with all necessary cofactors, in various buffers lacking a specific reagent ($Fe^{2+}$, ascorbate or DTT) and in the presence of N-oxalyl-glycine (NOG), a generic $Fe^{2+}$-2OG-dioxygenase inhibitor at a concentration of 0.5 mM. In addition to $Fe^{2+}$ (added in the form of $(NH_4)_2Fe(II)(SO_4)_2$) and 2OG, dithiothreitol (DTT) and sodium ascorbate were added to the reaction mixture: DTT is a reducing agent that helps to maintain $Fe^{2+}$.

Assay Components:
11.5 μM FTO
144 μM 2OG
16 μM $^{14}C$-2OG
80 μM $(NH_4)_2Fe(II)(SO_4)_2$
1 mM DTT
4 mM Ascorbate These were diluted to a total volume of 100 μl with 50 mM TRIS, pH 7.5. All reagents were mixed and pipetted into a 5 ml plastic screw cap tube, the FTO was added to the tube as a separate drop. A 500 μl Eppendorf tube containing 200 μl Hyamine hydroxide (Fisher Scientific, $CO_2$ trapping agent) was added to each tube and tubes were closed with a rubber septum. After incubation in an environmental shaker at 37° C. for half an hour, 200 μl methanol was added to the contents and the tubes were put on ice for 30 minutes to quench the reaction. The Eppendorf tubes containing the hyamine hydroxide were transferred to scintillation vials, mixed with 5 ml OptiPhase Liquid Scintillation Cocktail (Fisher Scientific) and total $^{14}C$ counts quantified using a Beckman L56500 Multi-Purpose Scintillation Counter.

Results of the first assay are shown in Table 1 below (whole counts—total starting 2-OG counts and in FIG. 4). The results reveal that FTO 2-OG turnover activity is stimulated by the cofactor Fe(II), and inhibited by N-oxalylglycine, which is an inhibitor of many 2-OG oxygenases. The activity is also stimulated by the addition of ascorbate which, as for other 2-OG oxygenases, may act as a surrogate for the natural substrate.

2OG uncoupled turnover assays with FTO, monitoring conversion of [1-14C]-2OG into [14C]-carbon dioxide, revealed that FTO catalysed 2OG decarboxylation, a reaction that was stimulated by ascorbate and FeSO4 (FIG. 8a). 2OG turnover was inhibited by known 2OG oxygenase inhibitors (FIG. 8b) and by the absence of Fe(II) and ascorbate.

TABLE 1

Results of 2-oxoglutarate decarboxylation assays

| | % whole counts | Average counts |
| --- | --- | --- |
| All assay components | 97.2 | 128559 |
| No Fe | 40.2 | 53152 |
| No Asc | 41.9 | 55413 |
| No DTT | 94.1 | 124389 |
| 0.5 mM NOG | 57.7 | 76266 |
| Whole counts | 100 | 132199 |

Example 5

Use of 2-OG Oxygenase Assay to Detect FTO Inhibitors

Using the method described in Example 4 various 2-OG oxygenase inhibitors were screened for their ability to inhibit activity FTO oxygenase activity. The inhibitors tested were:
NOG=N-oxalyl glycine
NOFD=N-oxalyl D-phenylalanine
P-2-4-CD—pyrdine-2,4-dicarboxylate
P-2-4-CD—pyrdine-2,5-dicarboxylate Compound 41 and Compound 16 have the structures set out below.

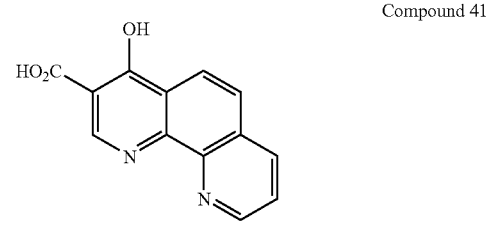

Compound 41

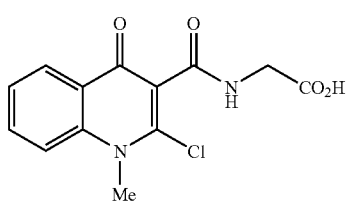

Compound 16

Example 6

Demethylation Assays

Using the method described in Example 2, but using only unlabelled 2OG, various potential substrates were screened for demethylation by FTO. The results are shown in FIGS. 5 and 6. The results demonstrate that, under the assay conditions used, FTO catalyses the demethylation of 3-methylthymine and 3-methylcytosine residues with a preference for 3 methylthymine residues.

Potential FTO substrates were screened including a synthetic single-stranded 1-methyl adenine (1-meA) methylated oligonucleotide, Lys-9 methylated histone H3, hypoxia inducible factor-1α (HIF-1α) subunit fragments, IκBα and coenzyme A derivatives. Only the 1-meA methylated oligonucleotide significantly stimulated turnover of 2OG (FIG. 6a). This activity was inhibited by N-oxalylglycine, fumarate and succinate, which were also inhibitors in the 2OG uncoupled turnover assays (FIG. 6c).

Using an LC-MS assay that directly monitors DNA demethylation (without the need for radiolabelled (co-)substrates or coupled assays), we demonstrated that FTO catalyses Fe(II)— and 2OG-dependent DNA demethylation. This activity was stimulated by ascorbate, as observed for other 2OG oxygenases (FIG. 6b).

Significantly reduced turnover was observed when the reaction was performed under reduced oxygen conditions. The production of succinate was verified by $^1$H NMR (400 MHz) analyses and that of formaldehyde was confirmed by derivatization with pentafluorophenylhydrazine.

To test the predicted role of the assigned Fe(II) binding and 2OG 5-carboxylate binding residues, His-304 and Arg-313 alanine substitution mutants were constructed. The His-304 mutant showed significantly reduced 2OG turnover whilst the Arg-313 mutant ablated activity (FIG. 6b).

FTO activity was further investigated using single-stranded oligonucleotides (ss-DNA) methylated at a single position: 1-methyladenine (1-meA), 1-methylguanine (1-meG), 3-methylcytosine (3-meC) and 3-methylthymine (3-meT) (FIG. 7b). Under the assay conditions at pH 7.5, FTO exhibited a preference for 3-meT over 1-meA or 3-meC in ss-DNA; 1-meG was not an FTO substrate (FIG. 7a). Consistent with prior reports, we found that recombinant forms of ABH2 and ABH3 exhibit a preference for 3-meC and 1-meA and 3-meT with the ss-DNA substrates, with only very low levels of 3-meT demethylation being observed under our conditions. The preference of FTO for 3-meT substrates was also observed in assays measuring the release of formaldehyde from methylated poly(dA) and poly(dT) (FIG. 7c).

Example 7

Localisation of FTO

Since FTO catalyses DNA demethylation, it was anticipated that it would be localised to the nucleus. Indeed, confocal imaging revealed that yellow fluorescent protein-tagged FTO (YFP-FTO) is concentrated in the nucleus, whereas YFP itself is present only in the cytoplasm. Interestingly, FTO localised to the nucleus even more effectively than ABH3.

2OG oxygenase catalysed post-translational hydroxylation is central to transcriptional regulation in the hypoxic response and 2OG oxygenases catalyse histone demethylation. The catalytic activity of FTO may similarly regulate the transcription of genes involved in metabolism by nucleic acid demethylation. Alternatively, it is possible that FTO, as proposed for ABH2, can act as a nucleic acid repair enzyme: there is evidence that breakdown of genomic repair processes leads to obesity and metabolic syndrome. Under the assay conditions used above at physiological pH, the preferred substrate of FTO identified was 3-methylthymine in DNA, a minor but stable lesion that is generated on exposure of DNA to methylating agents.

The invention claimed is:

1. A method for assaying FTO activity, the method comprising contacting a FTO polypeptide, with oxygen and 2-oxoglutarate as co-substrates and optionally a methylated nucleic acid substrate, and iron as a cofactor, and measuring oxygenase activity of said FTO polypeptide compared to a control, wherein said FTO polypeptide comprises:
   (a) the amino acid sequence of SEQ ID NO: 1,
   (b) an amino acid sequence having at least 80% identity to the amino acid sequence of SEQ ID NO: 1 over its full length, or
   (c) an amino acid sequence comprising amino acids 10 to 495 of SEQ ID NO: 1.

2. The method of claim 1, wherein oxygenase activity is measured in the presence of a reducing agent.

3. The method of claim 2, wherein the reducing agent is ascorbate, or an analogue thereof, a thiol or a phosphine.

4. The method of claim 1, wherein oxygenase activity is measured in the presence of the methylated nucleic acid substrate.

5. The method of claim 1, wherein the FTO polypeptide is a recombinant polypeptide.

6. The method of claim 1, wherein the FTO polypeptide comprises
   the amino acid sequence of SEQ ID NO: 1.

7. The method of claim 1, further comprising:
   (i) contacting the FTO polypeptide with a test agent;
   (ii) monitoring for oxygenase activity in the presence and absence of the test agent; and
   (iii) determining whether the test agent is an inhibitor or activator of FTO activity.

8. The method of claim 7, wherein the test agent is a reported inhibitor of a 2-OG oxygenase other than FTO, or an analogue or variant of such an inhibitor.

9. The method of claim 8, wherein the 2-OG oxygenase is procollagen prolyl or lysylhydroxylases, hypoxia inducible factor prolyl hydroxylase, methylated lysyl demethylase, asparaginyl hydroxylase, phosphatidyl serine receptor (Jmjd6), AlkB or human AlkB homologues and/or gibberellin C-20 oxidase.

10. The method of claim 8, wherein the inhibitor is an N-oxalyl amino acid, N-oxalylglycine or a derivative thereof, a glycine or alanine derivative, a 2-oxoacid analogue, a flavonoid or flavonoid derivative.

11. The method of claim 8, wherein the test agent comprises a metal ion.

12. The method of claim 7, wherein the test agent is a reducing agent.

13. The method of claim 12, wherein the reducing agent is a reported activator of a 2-OG oxygenase other than FTO.

14. The method of claim 12, wherein the reducing agent is ascorbate or an analogue of ascorbate, or a reducing agent of the dithiothreitol or phosphine chemical families.

15. The method of claim 7, further comprising: repeating all of the method steps using an enzyme other than FTO; and determining whether the test agent selectively inhibits or activates FTO or the other enzyme.

16. The method of claim 15, wherein the enzyme other than FTO is a 2-OG oxygenase.

17. The method of claim 16, wherein the 2-OG oxygenase is a hypoxia inducible factor hydroxylase, a collagen or procollagen prolyl hydroxylase, a nucleic acid demethylase, or a protein demethylase.

18. The method of claim 17, wherein the protein demethylase hydroxylates a methylated histone or a fragment thereof.

19. The method of claim 17, wherein the hypoxia inducible factor hydroxylase is a prolyl or asparaginyl hydroxylase, the nucleic acid demethylase is an AlkB homologue, and the protein demethylase is a tri-, di- or mono-methyl lysine or arginine residue demethylase.

20. The method of claim 1, wherein the methylated nucleic acid sequence is associated with a gene involved in weight modulation.

21. The method of claim 20, wherein the gene involved in weight modulation is the agouti gene or the neuropeptide Y gene.

22. The method of claim 1, further comprising:
   (i) contacting the FTO polypeptide with a test substrate;
   (ii) monitoring for oxygenase activity in the presence and absence of the test substrate; and
   (iii) determining whether the test substrate is a substrate of FTO.

23. The method of claim 22, wherein the test substrate is a human nucleic acid sequence.

24. The method of claim 23, wherein the nucleic acid sequence contains a 3-methylthymine base, a 1-methyladenine base or a 3-methylcytosine base.

\* \* \* \* \*